(12) United States Patent
Gouliaev et al.

(10) Patent No.: US 7,199,118 B2
(45) Date of Patent: Apr. 3, 2007

(54) BENZOTHIAZINE DERIVATIVES, THEIR PREPARATION AND USE

(75) Inventors: Alex Haahr Gouliaev, Vekso Sj (DK);
Morgens Larsen, Smorum (DK);
Thomas Varming, Ballerup (DK);
Claus Mathiesen, Ballerup (DK); Tina Holm Johansen, Ballerup (DK); Karin Sandager Nielsen, Ballerup (DK);
Barbara Hartz, Ballerup (DK); Jorgen Scheel-Kruger, Ballerup (DK)

(73) Assignee: NeuroSearch A/S, Ballerup (DK)

( * ) Notice: Subject to any disclaimer, the term of this patent is extended or adjusted under 35 U.S.C. 154(b) by 120 days.

(21) Appl. No.: 10/489,640

(22) PCT Filed: Oct. 2, 2002

(86) PCT No.: PCT/DK02/00654

§ 371 (c)(1),
(2), (4) Date: Mar. 15, 2004

(87) PCT Pub. No.: WO03/031422

PCT Pub. Date: Apr. 17, 2003

(65) Prior Publication Data

US 2004/0242571 A1 Dec. 2, 2004

(30) Foreign Application Priority Data

Oct. 10, 2001 (DK) .................. PA 2001 01498

(51) Int. Cl.
*C07D 417/04* (2006.01)
*C07D 417/14* (2006.01)
*C07D 279/34* (2006.01)
*A61K 31/5415* (2006.01)

(52) U.S. Cl. .................. 514/226.5; 544/6; 544/49; 540/575; 514/218

(58) Field of Classification Search .................. 544/6, 544/49; 514/226.5, 218; 540/575
See application file for complete search history.

(56) References Cited

U.S. PATENT DOCUMENTS

| 3,113,075 A | * 12/1963 | Bicking et al. .......... 514/226.5 |
| 3,284,450 A | 11/1966 | Kraaijeveld et al. |
| 2002/0013313 A1 | 1/2002 | Winter et al. |

FOREIGN PATENT DOCUMENTS

| FR | 1552763 | * 11/1963 |
| FR | 3 136 M | 2/1965 |
| WO | 99 42456 A | 8/1999 |
| WO | 01 57045 A | 8/2001 |

OTHER PUBLICATIONS

An English abstract and STN printout for U.S. Appl. No. 3,113,075.*
Zinnes et al. Journal of Organic Chemistry (1966), 31(1), 162-5.*
Sianesi et al. Chemische Berichte (1971), 104(6), 1880-91.*

* cited by examiner

*Primary Examiner*—Kahsay Habte
(74) *Attorney, Agent, or Firm*—Birch, Stewart, Kolasch & Birch, LLP

(57) ABSTRACT

This invention relates to novel benzothiazine derivatives of Formula I useful as modulators of the AMPA sensitive glutamate receptors, pharmaceutical compositions comprising such compounds and their use in therapy.

13 Claims, 8 Drawing Sheets

BENZOTHIAZINE DERIVATIVES, THEIR PREPARATION AND USE

TECHNICAL FIELD

This invention relates to novel benzothiazine derivatives useful as modulators of the AMPA sensitive glutamate receptors, pharmaceutical compositions comprising such compounds and their use in therapy.

BACKGROUND ART

L-Glutamate is the major excitatory neurotransmitter in the mammalian central nervous system, which activates several subtypes of ionotropic and metabotropic receptors. The ionotropic receptors can be divided into three subtypes, which are defined by the depolarizing actions of the selective agonists N-methyl-D-aspartate (NMDA), alpha-amino-3-hydroxy-5-methylisoxazole-4-propionic acid (AMPA), and kainic acid (KA).

AMPA receptors are assembled from four protein sub-units known as GluR1 to GluR4, while kainic acid receptors are assembled from the sub-units GluR5 to GluR7, and KA-1 and KA-2.

AMPA receptors have been associated with diseases and conditions as diverse as memory and learning disorders, a psychotic disorder, sexual dysfunction, an intellectual impairment disorder, schizophrenia, depression, autism, Alzheimer's disease, learning deficit, attention deficit, memory loss, and senile dementia, or from a disorder or disease resulting from trauma, from stroke, from epilepsy, from Alzheimer's disease, from a neurotoxic agent, from aging, from a neurodegenerative disorder, from alcohol intoxication, from substance abuse, from cardiac bypass surgery or from cerebral ischemia.

SUMMARY OF THE INVENTION

It is an object of the present invention to provide new benzothiazine derivatives useful as modulators of the AMPA sensitive glutamate receptors. The compounds of the present invention show excellent stability without loss of in vitro or in vivo activity. In fact the compounds of the present invention are potent and highly efficacious in potentiating AMPA-responses, show good lipophilicity and hence have good physicochemical properties, in particular ability to cross the blood/brain barrier.

Accordingly, in its first aspect, the invention provides benzothiazine derivatives of Formula I

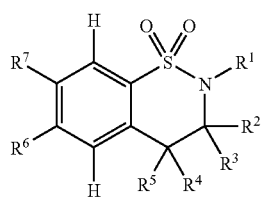

(I)

any of its enantiomers or any mixture of its enantiomers, or a pharmaceutically acceptable salt thereof, wherein $R^1$ represents hydrogen, alkyl, alkenyl, alkynyl, cycloalkyl, cycloalkenyl, aryl or heteroaryl; and $R^2$ and $R^3$, independently of each another, represent hydrogen, alkyl (other than t-butyl), alkenyl, alkynyl, cycloalkyl, cycloalkenyl, and/or a saturated or partially saturated mono- or bi-cyclic heterocyclic ring; or $R^2$ and $R^3$, together with the carbon atom to which they are attached, form a saturated or partially saturated monocyclic (spiro) carbocyclic ring; or $R^2$ and/or $R^3$, together with $R^4$ and/or $R^5$, form a saturated, or partially saturated monocyclic carbocyclic ring; and $R^4$ and $R^5$, independently of each another, represent hydrogen, alkyl, alkenyl, alkynyl, cycloalkyl, cycloalkenyl, and/or a saturated or partially saturated mono- or bi-cyclic heterocyclic ring; or $R^4$ and $R^5$, together with the carbon atom to which they are attached, form a saturated or partially saturated monocyclic carbocyclic (spiro) ring; or $R^6$ represents hydrogen, halogen, alkyl, cycloalkyl, haloalkyl or alkoxy; and $R^7$ represents hydrogen, alkyl, cycloalkyl, hydroxyalkyl, alkenyl, alkynyl or halogen, or a group of the formula
—$R^{10}$—$NR^9R^8$, —$R^{10}$—$NO_2$, —$R^{10}$—$OR^8$, —$R^{10}$—$SR^8$, —$R^{10}$—$S(=O)NR^9R^8$, —$R^{10}$—$S(=O)R^8$, —$R^{10}$—$S(=O)_2R^8$, —$R^{10}$—$S(=O)_2OR^8$, —$R^{10}$—$S(=O)_2NR^9R^8$, —$R^{10}$—$NR^9S(=O)_2R^8$, —$R^{10}$—$NR^{11}S(=O)_2NR^9R^8$, —$R^{10}$—$CN$, —$R^{10}$—$C(=NR^9)R^8$, —$R^{10}$—$C(=NNR^9)R^8$, —$R^{10}$—$C(=NOR^9)R^8$, —$R^{10}$—$C(=O)R^8$, —$R^{10}$—$C(=O)NR^9R^8$, —$R^{10}$—$C(=S)R^8$, —$R^{10}$—$C(=O)OR^8$, —$R^{10}$—$C(=S)OR^8$, —$R^{10}$—$C(=O)SR^8$, —$R^{10}$—$C(=S)SR^8$, —$R^{10}$—$C(=O)NR^9(OR^8)$, —$R^{10}$—$C(=S)NR^9(OR^8)$, —$R^{10}$—$C(=O)NR^9(SR^8)$, —$R^{10}$—$C(=S)NR^9(SR^8)$, —$R^{10}$—$CH(CN)_2$, —$R^{10}$—$C(=O)NR^9R^8$, —$R^{10}$—$NR^9C(=O)R^8$, —$R^{10}$—$NR^{11}C(=O)NR^9R^8$, —$R^{10}$—$C(=S)NR^9R^8$, —$R^{10}$—$CH[C(=O)R^8]_2$, —$R^{10}$—$CH[C(=S)R^8]_2$, —$R^{10}$—$CH[C(=O)OR^8]_2$, —$R^{10}$—$CH[C(=S)OR^8]_2$, —$R^{10}$—$CH[C(=O)SR^8]_2$, —$R^{10}$—$CH[C(=S)SR^8]_2$, or —$R^{10}$—$CH[C(=S)NR^9R_8]_2$; wherein
$R^8$, $R^9$ and $R^{11}$, independently of each another, represent hydrogen, alkyl, alkenyl, alkynyl, cycloalkyl, alkoxy, hydroxy, aryl or heteroaryl, which aryl or heteroaryl may optionally be substituted one or more times with alkyl, cycloalkyl, alkoxy, halogen, hydroxy, amino, trifluoromethyl, trifluoromethoxy or nitro; or $R^8$ and $R^9$, together with the atoms to which they are bound, form a heterocyclic ring, which heterocyclic ring may optionally be substituted one or more times with alkyl, cycloalkyl, alkoxy, halogen, hydroxy, amino, trifluoromethyl, trifluoromethoxy or nitro, and $R^{11}$ is as defined above; and $R^{10}$ is absent or represents a linker selected from alkyl, alkenyl, alkynyl, cycloalkyl, aryl or heteroaryl; or $R^7$ represents represents a mono- or polycyclic carbocyclic or heterocyclic group, which carbocyclic or heterocyclic group may optionally be substituted one or more times with substituents selected from alkyl, cycloalkyl, hydroxyalkyl, alkenyl, alkynyl or halogen, or a group of the formula
—$R^{10}$—$NR^9R^8$, —$R^{10}$—$NO_2$, —$R^{10}$—$OR^8$, —$R^{10}$—$SR^8$, —$R^{10}$—$S(=O)NR^9R^8$, —$R^{10}$—$S(=O)R^8$, —$R^{10}$—$S(=O)_2R^8$, —$R^{10}$—$S(=O)_2OR^8$, —$R^{10}$—$S(=O)_2NR^9R^8$, —$R^{10}$—$NR^9S(=O)_2R^8$, —$R^{10}$—$NR^{11}S(=O)_2NR^9R^8$, —$R^{10}$—$CN$, —$R^{10}$—$C(=NR^9)R^8$, —$R^{10}$—$C(=NNR^9)R^8$, —$R^{10}$—$C(=NOR^9)R^8$, —$R^{10}$—$C(=O)R^8$, —$R^{10}$—$C(=O)NR^9R^8$, —$R^{10}$—$C(=S)R^8$, —$R^{10}$—$C(=O)OR^8$, —$R^{10}$—$C(=S)OR^8$, —$R^{10}$—$C(=O)SR^8$, —$R^{10}$—$C(=S)SR^8$, —$R^{10}$—$C(=O)NR^9(OR^8)$, —$R^{10}$—$C(=S)NR^9(OR^8)$, —$R^{10}$—$C(=O)NR^9(SR^8)$, —$R^{10}$—$C(=S)NR^9(SR^8)$, —$R^{10}$—$CH(CN)_2$, —$R^{10}$—$C(=O)NR^9R^8$, —$R^{10}$—

NR$^9$C(=O)R$^8$, —R$^{10}$—NR$^{11}$C(=O)NR$^9$R$^8$, —R$^{10}$—C(=S)NR$^9$R$^8$, —R$^{10}$—CH[C(=O)R$^8$]$_2$, —R$^{10}$—CH[C(=S)R$^8$]$_2$, —R$^{10}$—CH[C(=O)OR$^8$]$_2$, —R$^{10}$—CH[C(=S)OR$^8$]$_2$, —R$^{10}$—CH[C(=O)SR$^8$]$_2$, —R$^{10}$—CH[C(=S)SR$^8$]$_2$, or —R$^{10}$—CH[C(=S)NR$^9$R$^8$]$_2$; wherein R$^8$, R$^9$ and R$^{11}$, independently of each another, represent hydrogen, alkyl, alkenyl, alkynyl, cycloalkyl, alkoxy, hydroxy, aryl or heteroaryl, which aryl or heteroaryl may optionally be substituted one or more times with alkyl, cycloalkyl, alkoxy, halogen, hydroxy, amino, trifluoromethyl, trifluoromethoxy or nitro; or R$^8$ and R$^9$, together with the atoms to which they are bound, form a heterocyclic ring, which heterocyclic ring may optionally be substituted one or more times with alkyl, cycloalkyl, alkoxy, halogen, hydroxy, amino, trifluoromethyl, trifluoromethoxy or nitro, and R$^{11}$ is as defined above; and R$^{10}$ is absent or represents a linker selected from alkyl, alkenyl, alkynyl, cycloalkyl, aryl or heteroaryl.

In another aspect, the invention provides pharmaceutical compositions comprising a therapeutically effective amount of a benzothiazine derivative of the invention, or a pharmaceutically acceptable addition salt thereof, together with at least one pharmaceutically acceptable carrier or diluent.

In a third aspect, the invention relates to the use of a benzothiazine derivative of the invention, or a pharmaceutically acceptable addition salt thereof, for the manufacture of a pharmaceutical composition for the treatment, prevention or alleviation of a disease or a disorder or a condition of a mammal, including a human, which disease, disorder or condition is responsive to modulation of the AMPA receptor complex of the central nervous system.

In a further aspect, the invention provides methods for the treatment, prevention or alleviation of diseases, disorders or conditions of living animal bodies, including humans, which disorders, diseases or conditions are responsive to modulation of the AMPA receptor complex of the central nervous system, which method comprises the step of administering to such a living animal body, including a human, in need thereof a therapeutically effective amount of a benzothiazine derivative of the invention.

Other objects of the invention will be apparent to the person skilled in the art from the following detailed description and examples.

DETAILED DISCLOSURE OF THE INVENTION

In its first aspect the present invention provides new benzothiazine derivatives represented by Formula I

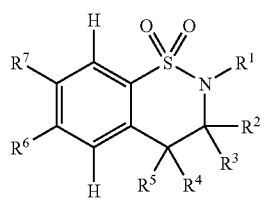

any of its enantiomers or any mixture of its enantiomers, or a pharmaceutically acceptable salt thereof,
wherein
R$^1$ represents hydrogen, alkyl, alkenyl, alkynyl, cycloalkyl, cycloalkenyl, aryl or heteroaryl; and R$^2$ and R$^3$, independently of each another, represent hydrogen, alkyl other than t-butyl, alkenyl, alkynyl, cycloalkyl, cycloalkenyl, and/or a saturated or partially saturated mono- or bi-cyclic heterocyclic ring; or R$^2$ and R$^3$, together with the carbon atom to which they are attached, form a saturated or partially saturated monocyclic (spiro) carbocyclic ring; or R$^2$ and R$^3$, together with R$^4$ and/or R$^5$, form a saturated or partially saturated monocyclic carbocyclic ring; and R$^4$ and R$^5$, independently of each another, represent hydrogen, alkyl, alkenyl, alkynyl, cycloalkyl, cycloalkenyl, and/or a saturated or partially saturated mono- or bi-cyclic heterocyclic ring; or R$^4$ and R$^5$, together with the carbon atom to which they are attached, form a saturated or partially saturated monocyclic carbocyclic (spiro) ring; or R$^4$ and R$^5$, together with R$^2$ and/or R$^3$, form a saturated monocyclic carbocyclic ring; and R$^6$ represents hydrogen, halogen, alkyl, cycloalkyl, haloalkyl or alkoxy; and R$^7$ represents hydrogen, alkyl, cycloalkyl, hydroxyalkyl, alkenyl, alkynyl or halogen, or a group of the formula
—R$^{10}$—NR$^9$R$^8$, —R$^{10}$—NO$_2$, —R$^{10}$—OR$^8$, —R$^{10}$—SR$^8$, —R$^{10}$—S(=O)NR$^9$R$^8$, —R$^{10}$—S(=O)R$^8$, —R$^{10}$—S(=O)$_2$R$^8$, —R$^{10}$—S(=O)$_2$OR$^8$, —R$^{10}$—S(=O)$_2$NR$^9$R$^8$, —R$^{10}$—NR$^9$S(=O)$_2$R$^8$, —R$^{10}$—NR$^{11}$S(=O)$_2$NR$^9$R$^8$, —R$^{10}$—CN, —R$^{10}$—C(=NR$^9$)R$^8$, —R$^{10}$—C(=NNR$^9$)R$^8$, —R$^{10}$—C(=NOR$^9$)R$^8$, —R$^{10}$—C(=O)R$^8$, —R$^{10}$—C(=O)NR$^9$R$^8$, —R$^{10}$—C(=S)R$^8$, —R$^{10}$—C(=O)OR$^8$, —R$^{10}$—C(=S)OR$^8$, —R$^{10}$—C(=O)SR$^8$, —R$^{10}$—C(=S)SR$^8$, —R$^{10}$—C(=O)NR$^9$(OR$^8$), —R$^{10}$—C(=S)NR$^9$(OR$^8$), —R$^{10}$—C(=O)NR$^9$(SR$^8$), —R$^{10}$—C(=S)NR$^9$(SR$^8$), —R$^{10}$—CH(CN)$_2$, —R$^{10}$—C(=O)NR$^9$R$^8$, —R$^{10}$—NR$^9$C(=O)R$^8$, —R$^{10}$—NR$^{11}$C(=O)NR$^9$R$^8$, —R$^{10}$—C(=S)NR$^9$R$^8$, —R$^{10}$—CH[C(=O)R$^8$]$_2$, —R$^{10}$—CH[C(=S)R$^8$]$_2$, —R$^{10}$—CH[C(=O)OR$^8$]$_2$, —R$^{10}$—CH[C(=S)OR$^8$]$_2$, —R$^{10}$—CH[C(=O)SR$^8$]$_2$, —R$^{10}$—CH[C(=S)SR$^8$]$_2$, or —R$^{10}$—CH[C(=S)NR$^9$R$^8$]$_2$; wherein R$^8$, R$^9$ and R$^{11}$, independently of each another, represent hydrogen, alkyl, alkenyl, alkynyl, cycloalkyl, alkoxy, hydroxy, aryl or heteroaryl, which aryl or heteroaryl may optionally be substituted one or more times with alkyl, cycloalkyl, alkoxy, halogen, hydroxy, amino, trifluoromethyl, trifluoromethoxy or nitro; or R$^8$ and R$^9$, together with the atoms to which they are bound, form a heterocyclic ring, which heterocyclic ring may optionally be substituted one or more times with alkyl, cycloalkyl, alkoxy, halogen, hydroxy, amino, trifluoromethyl, trifluoromethoxy or nitro, and R$^{11}$ is as defined above; and R$^{10}$ is absent or represents a linker selected from alkyl, alkenyl, alkynyl, cycloalkyl, aryl or heteroaryl; or R$^7$ represents represents a mono- or polycyclic carbocyclic or heterocyclic group, which carbocyclic or heterocyclic group may optionally be substituted one or more times with substituents selected from alkyl, cycloalkyl, hydroxyalkyl, alkenyl, alkynyl or halogen, or a group of the formula
—R$^{10}$—NR$^9$R$^8$, —R$^{10}$—NO$_2$, —R$^{10}$—OR$^8$, —R$^{10}$—SR$^8$, —R$^{10}$—S(=O)NR$^9$R$^8$, —R$^{10}$—S(=O)R$^8$, —R$^{10}$—S(=O)$_2$R$^8$, —R$^{10}$—S(=O)$_2$OR$^8$, —R$^{10}$—S(=O)$_2$NR$^9$R$^8$, —R$^{10}$—NR$^9$S(=O)$_2$R$^8$, —R$^{10}$—NR$^{11}$S(=O)$_2$NR$^9$R$^8$, —R$^{10}$—CN, —R$^{10}$—C(=NR$^9$)R$^8$, —R$^{10}$—C(=NNR$^9$)R$^8$, —R$^{10}$—C(=NOR$^9$)R$^8$, —R$^{10}$—C(=O)R$^8$, —R$^{10}$—C(=O)NR$^9$R$^8$, —R$^{10}$—C(=S)R$^8$, —R$^{10}$—C(=O)OR$^8$, —R$^{10}$—C(=S)OR$^8$, —R$^{10}$—C(=O)SR$^8$, —R$^{10}$—C(=S)SR$^8$, —R$^{10}$—C(=O)NR$^9$(OR$^8$), —R$^{10}$—C(=S)NR$^9$(OR$^8$), —R$^{10}$—C(=O)NR$^9$(SR$^8$), —R$^{10}$—C(=S)NR$^9$ (SR$^8$), —R$^{10}$—CH(CN)$_2$, —R$^{10}$—C(=O)NR$^9$R$^8$, —R$^{10}$—NR$^9$C(=O)R$^8$, —R$^{10}$—NR$^{11}$C(=O)NR$^9$R$^8$, —R$^{10}$—C(=S)NR$^9$R$^8$, —R$^{10}$—CH[C(=O)R$^8$]$_2$, —R$^{10}$—CH[C(=S)R$^8$]$_2$, —R$^{10}$—CH[C(=O)OR$^8$]$_2$, —R$^{10}$—CH[C(=S)OR$^8$]$_2$, —R$^{10}$—CH[C(=O)SR$^8$]$_2$, —R$^{10}$—CH[C(=S)SR$^8$]$_2$, or —R$^{10}$—CH[C(=S)NR$^9$R$^8$]$_2$; wherein R$^8$, R$^9$ and R$^{11}$, independently of each another, represent hydrogen, alkyl, alkenyl, alkynyl, cycloalkyl, alkoxy, hydroxy, aryl or heteroaryl, which aryl or heteroaryl may optionally be substituted one or more times with alkyl, cycloalkyl, alkoxy, halogen, hydroxy, amino, trifluoromethyl, trifluoromethoxy or nitro; or R$^8$ and R$^9$, together with the atoms to which they are bound, form a heterocyclic ring, which heterocyclic ring may optionally be substituted one or more times with alkyl, cycloalkyl, alkoxy, halogen, hydroxy, amino, trifluoromethyl, trifluoromethoxy or nitro, and R$^{11}$ is as defined above; and R$^{10}$ is absent or represents a linker selected from alkyl, alkenyl, alkynyl, cycloalkyl, aryl or heteroaryl.

In a more preferred embodiment, R$^1$ represents hydrogen, alkyl or cycloalkyl.

In an even more preferred embodiment R$^1$ represents hydrogen.

In another preferred embodiment R$^2$ or R$^3$ represent hydrogen, and the other of R$^2$ and R$^3$ represent alkyl other than t-butyl, alkenyl, alkynyl, cycloalkyl, cycloalkenyl, and/or a saturated or partially saturated mono- or bi-cyclic heterocyclic ring.

In a more preferred embodiment, R$^2$ or R$^3$ represent cycloalkyl or cycloalkenyl; and the other of R$^2$ and R$^3$ represent hydrogen or alkyl.

In an even more preferred embodiment, R$^2$ or R$^3$ represent cycloalkyl; and the other of R$^2$ and R$^3$ represent hydrogen.

In a third preferred embodiment, R$^2$ and R$^3$ together with the carbon atom to which they are attached form a carbocyclic, saturated (spiro) ring, holding of from 5 to 7 carbon atoms.

In a more preferred embodiment, R$^2$ or R$^3$, or R$^4$ or R$^5$, respectively, represent a saturated mono- or bi-cyclic heterocyclic ring having N, O and/or S as heteroatom; and the other of R$^2$ and R$^3$, or R$^4$ and R$^5$, respectively, represent hydrogen, alkyl or cycloalkyl.

In an even more preferred embodiment, R$^2$ or R$^3$, or R$^4$ or R$^5$, respectively, represent pyrrolidinyl, pyrazolidinyl, imidazolidinyl, piperidinyl, morpholinyl, thiomorpholinyl or piperazinyl; and the other of R$^2$ and R$^3$, or R$^4$ and R$^5$, respectively, represent hydrogen or alkyl.

In a yet more preferred embodiment, R$^4$ and R$^5$ both represent hydrogen.

In a fourth preferred embodiment, R$^6$ represents hydrogen or alkyl.

In a fifth preferred embodiment R$^7$ represents —R$^{10}$—S(=O)$_2$R$^8$, —R$^{10}$—S(=O)$_2$OR$^8$, —R$^{10}$—S(=O)$_2$NR$^9$R$^8$, or —R$^{10}$—NR$^9$S(=O)$_2$R$^8$; wherein R$^8$ represents hydrogen or alkyl, and R$^9$ represents hydrogen or alkyl; or R$^8$ and R$^9$ together with the nitrogen and/or sulphur atoms to which they are bound, form a pyrrolidine-, a piperidine-, a piperazine-, a homopiperazine-, or a morpholine ring, which heterocyclic ring is optionally substituted with alkyl or hydroxy; and R$^{10}$ is absent or represents alkyl.

In a more preferred embodiment, R$^7$ represents an N,N-dimethylamine-1-sulfonyl group; a piperidine-1-sulfonyl group; a 4-methyl-piperazine-1-sulfonyl group; a morpholine-4-sulfonyl group; or a 4-hydroxypiperidine-1-sulfonyl group.

In a more preferred embodiment, the benzothiazine derivative is (3RS)-3-Cyclohexyl-7-(piperidine-1-sulfonyl)-3,4-dihydro-2H-benzo[e][1,2]thiazine-1,1-dioxide;

(3RS)-3-Cyclopentyl-7-(piperidine-1-sulfonyl)-3,4-dihydro-2H-benzo[e][1,2]thiazine-1,1-dioxide;

(3RS)-3-Cyclohexyl-7-(4-methyl-piperazine-1-sulfonyl)-3,4-dihydro-2H-benzo[e][1,2]thiazine-1,1-dioxide;

(3RS)-3-Cyclohexyl-7-(4-methyl-piperazine-1-sulfonyl)-3,4-dihydro-2H-benzo[e][1,2]thiazine-1,1-dioxide;

(3RS)-3-Cyclopentyl-6-methyl-7-(piperidine-1-sulfonyl)-3,4-dihydro-2H-benzo[e][1,2]thiazine-1,1-dioxide;

(3RS)-3-Cyclopentyl-6-methyl-7-(morpholine-4-sulfonyl)-3,4-dihydro-2H-benzo[e][1,2]thiazine-1,1-dioxide;

(3RS)-3-Cyclopentyl-6-methyl-7-(4-methyl-piperazine-1-sulfonyl)-3,4-dihydro-2H-benzo[e][1,2]thiazine-1,1-dioxide;

(3RS)-3-Cyclopentyl-6-methyl-7-(N,N-dimethylamine-1-sulfonyl)-3,4-dihydro-2H-benzo[e][1,2]thiazine-1,1-dioxide;

(3RS)-3-Cyclopentyl-6-methyl-7-(4-hydroxypiperidine-1-sulfonyl)-3,4-dihydro-2H-benzo[e][1,2]thiazine-1,1-dioxide;

(3RS)-3-Cyclopentyl-7-(N,N-dimethylamine-1-sulfonyl)-3,4-dihydro-2H-benzo[e][1,2]thiazine-1,1-dioxide;

(3RS)-3-Cyclopentyl-7-(morpholine-1-sulfonyl)-3,4-dihydro-2H-benzo[e][1,2]thiazine-1,1-dioxide;

[1-(3-Cyclopentyl-1,1-dioxo-1,2,3,4-tetrahydro-1 16-benzo[e][1,2]thiazine-7-sulfonyl)piperidein-4-yl]-dimethyl-amine; or any of the spiro compounds disclosed in Example 17 as Compound Nos. 33a–l;

or a pharmaceutically acceptable salt thereof.

Definition of Substituents

In the context of this invention halogen represents a fluorine, a chlorine, a bromine or an iodine atom.

In the context of this invention a haloalkyl group designates a univalent saturated, straight or branched hydrocarbon chain (i.e. alkyl group), which hydrocarbon chain is substituted one or more times with halogen. Preferred haloalkyl groups of the invention include trihalogenmethyl. Thus, a trihalogenmethyl group represents e.g. a trifluoromethyl group, a trichloromethyl group and similar trihalogen-substituted methyl groups.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to eight carbon atoms ($C_{2-8}$-alkenyl), more preferred of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butdienyl; 1-, 2-, 3-, 4- or 5-hexenyl, or 1,3-hexdienyl, or 1,3,5-hextrienyl; 1-, 2-, 3-, 4-, 5-, 6-, or 7-octenyl, or 1,3-octdienyl, or 1,3,5-octtrienyl, or 1,3,5,7-octtetraenyl.

In the context of this invention an alkynyl group designates a carbon chain containing one or more triple bonds, including di-ynes, tri-ynes and poly-ynes. In a preferred embodiment the alkynyl group of the invention comprises of from two to eight carbon atoms ($C_{2-8}$-alkynyl), more preferred of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butdiynyl; 1-, 2-, 3-, 4-pentynyl, or 1,3-pentdiynyl; 1-, 2-, 3-, 4-, or 5-henynyl, or 1,3-hexdiynyl or 1,3,5-hextriynyl; 1-, 2-, 3-, 4-, 5- or 6-heptynyl, or 1,3-heptdiynyl, or 1,3,5-hepttriynyl; 1-, 2-, 3-, 4-, 5-, 6- or 7-octynyl, or 1,3-octdiynyl, or 1,3,5-octtriynyl, or 1,3,5,7-octtetraynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkenyl group designates a cyclic alkenyl group, preferably containing of from three to seven carbon atoms ($C_{3-7}$-cycloalkenyl), including cyclopentenyl, cyclohexenyl and cycloheptenyl.

In the context of this invention an alkoxy group designates an "alkyl-O—" group, wherein alkyl is as defined above.

In the context of this invention a hydroxyalkyl group designates a "HO-alkyl-" group, wherein alkyl is as defined above. Preferred hydroxyalkyl groups of the invention include hydroxymethyl, 1-hydroxy-ethyl and 2-hydroxy-ethyl.

In the context of this invention a saturated or partially saturated monocyclic (spiro) carbocyclic ring designates a monocyclic carbocyclic ring holding carbon only as ring atom. The ring structure may be saturated or partially saturated. Preferred saturated carbocyclic (cycloalkyl) groups of the invention include cyclopentyl, cyclohexyl, cycloheptyl and norbornan (bicyclo[2.2.1]heptan). Preferred partially saturated carbocyclic groups of the invention include the cyclopentenyl, cyclohexenyl, cycloheptenyl and norbornen (bicyclo[2.2.1]bent-2-en).

In the context of this invention a saturated or partially saturated monocyclic carbocyclic ring designates a monocyclic carbocyclic ring holding carbon only as ring atom. Preferred saturated carbocyclic groups of the invention include cyclopentyl, cyclohexyl, cycloheptyl and norbornan (bicyclo[2.2.1]heptan). Preferred partially saturated carbocyclic groups of the invention include cyclopentenyl, cyclohexenyl, cycloheptenyl and norbornen (bicyclo[2.2.1]hent-2-en).

In the context of this invention a saturated or partially saturated mono- or bi-cyclic heterocyclic ring designates a mono- or bi-cyclic ring, which holds one or more heteroatoms in its ring structure. Preferred heteroatoms include nitrogen (N), oxygen (O), and sulphur (S). The ring may in particular be fully saturated or partially saturated.

Preferred saturated monocyclic heterocyclic rings include pyrrolidone, 1,3-dioxolane, imidazolidine, pyrazolidine, piperidine, homopiperidine, morpholine, thiomorpholine, piperazine and homopiperazine.

Preferred saturated bicyclic heterocyclic rings include tropane.

Preferred partially saturated bicyclic heterocyclic rings include tropene.

In the context of this invention an aryl group designates a monocyclic or polycyclic aromatic hydrocarbon group. Examples of preferred aryl groups of the invention include phenyl, indenyl, naphthyl, azulenyl, fluorenyl, and anthracenyl.

In the context of this invention a heteroaryl group designates an aromatic mono-, bi- or poly-heterocyclic group, which holds one or more heteroatoms in its ring structure. Preferred heteroatoms include nitrogen (N), oxygen (O), and sulphur (S). Preferred heterocyclic monocyclic groups of the invention include 5- and 6 membered heterocyclic monocyclic groups. Examples of preferred aromatic monocyclic heteroaryl groups of the invention include furanyl, in particular 2- or 3-furanyl; thienyl, in particular 2 or 3-thienyl; pyrrolyl (azolyl), in particular 1,2 or 3-pyrrolyl; oxazolyl, in particular oxazol-2,4 or 5-yl; thiazolyl, in particular thiazol-2,4 or 5-yl; imidazolyl, in particular 1,2 or 4-imidazolyl; pyrazolyl, in particular 1,3 or 4-pyrazolyl; isoxazolyl, in particular isoxazol-3,4 or 5-yl; isothiazolyl, in particular isothiazol-3,4 or 5-yl; oxadiazolyl, in particular 1,2,3-, 1,2,4-, 1,2,5- or 1,3,4-oxadiazol-3,4 or 5-yl; triazolyl, in particular 1,2,3-, 1,2,4-, 2,1,3- or 4,1,2-triazolyl; thiadiazolyl, in particular thiadiazol-3,4 or 5-yl; pyridinyl, in particular 2,3 or 4-pyridinyl; pyridazinyl, in particular 3 or 4-pyridazinyl; pyrimidinyl, in particular 2,4 or 5-pyrimidinyl; pyrazinyl, in particular 2 or 3-pyrazinyl; triazinyl, in particular 1,2,3-, 1,2,4- or 1,3,5-triazinyl; and tetrazolyl, in particular 1,2,3,4- or 2,1,3,4-tetrazolyl.

Most preferred monocyclic heteroaryl groups of the invention include 1,2 or 3-pyrrolyl (azolyl); 1-, 2- or 3-pyridinyl; and 2,4 or 5-pyrimidinyl.

Examples of preferred bicyclic aromatic heteroaryl groups of the invention include indolizinyl, in particular 2,5 or 6-indolizinyl; indolyl, in particular 2,5 or 6-indolyl; isoindolyl, in particular 2,5 or 6-isoindolyl; benzofuranyl, in particular 2,5 or 6-benzofuranyl; benzothienyl, in particular 2,5 or 6-benzothienyl; benzimidazolyl, in particular 2,5 or 6-benzimidazolyl; benzothiazolyl, in particular 5 or 6-benzothiazolyl; purinyl, in particular 2 or 8-purinyl; quinolinyl, in particular 2,3,6 or 7-quinolinyl; isoquinolinyl, in particular 3,6 or 7-isoquinolinyl; cinnolinyl, in particular 6 or 7-cinnolinyl; phthalazinyl, in particular 6 or 7-phthalazinyl; quinazolinyl, in particular 2,6 or 7-quinazolinyl; quinoxalinyl, in particular 2 or 6-quinoxalinyl; 1,8-naphthyridinyl, in particular 1,8-naphthyridin-2,3,6 or 7-yl; and pteridinyl, in particular 2,6 or 7-pteridinyl.

Most preferred bicyclic heteroaryl groups of the invention include 2,3,6 or 7-quinolinyl; and 3,6 or 7-isoquinolinyl.

Examples of preferred tricyclic aromatic heteroaryl groups of the invention include acridinyl, in particular 2,3,6 or 7-acridinyl; carbazolyl, in particular 2,3,6 or 7-carbazolyl; phenazinyl, in particular 2,3,7 or 8-phenazinyl; phenothiazinyl, in particular 2,3,7 or 8-phenothiazinyl; and phenoxazinyl, in particular 2,3,7 or 8-phenoxazinyl.

Pharmaceutically Acceptable Salts

The benzothiazine derivatives of the invention may be provided in any form suitable for the intended administration. Suitable forms include pharmaceutically.(i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphthalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a benzothiazine derivative of the invention and its pharmaceutically acceptable acid addition salt.

Metal salts of a benzothiazine derivative of the invention includes alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Steric Isomers

The benzothiazine derivatives of the present invention may exist in (+) and (−) forms as well as in racemic forms (±). The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes,. e.g., by fractional crystallisation of d- or l- (tartrates, mandelates, or camphorsulphonate) salts for example.

The benzothiazine derivatives of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Preparation

The benzothiazine derivatives of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Pharmaceutical Compositions

In another aspect the invention provides novel pharmaceutical compositions comprising a therapeutically effective amount of the benzothiazine derivative of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the benzothiazine derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to modulation of the AMPA receptor complex of the central nervous system, and which method comprises administering to such a living animal body, including a human, in need thereof an effective amount of a benzothiazine derivative of the invention.

In a more preferred embodiment, the invention provides a method of treating a disease, disorder or condition selected from the group consisting of memory and learning disorders, psychotic disorders, sexual dysfunction, amyotrophic lateral sclerosis (ALS), multiple schlerosis (MS), intellectual impairment disorders, schizophrenia, depression, autism, Alzheimer's disease, learning deficit, attention deficit hyperactivity disorder (ADHD), memory loss, senile dementia, disorders or disease resulting from trauma, stroke, epilepsy, Alzheimer's disease, neurotoxic agents, aging, neurodegenerative disorder, alcohol intoxication, substance abuse, cardiac bypass surgery, and cerebral ischaemia.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

BRIEF DESCRIPTION OF THE DRAWINGS

The present invention is further illustrated by reference to the accompanying drawing, in which.

EXAMPLES

Figure 1:
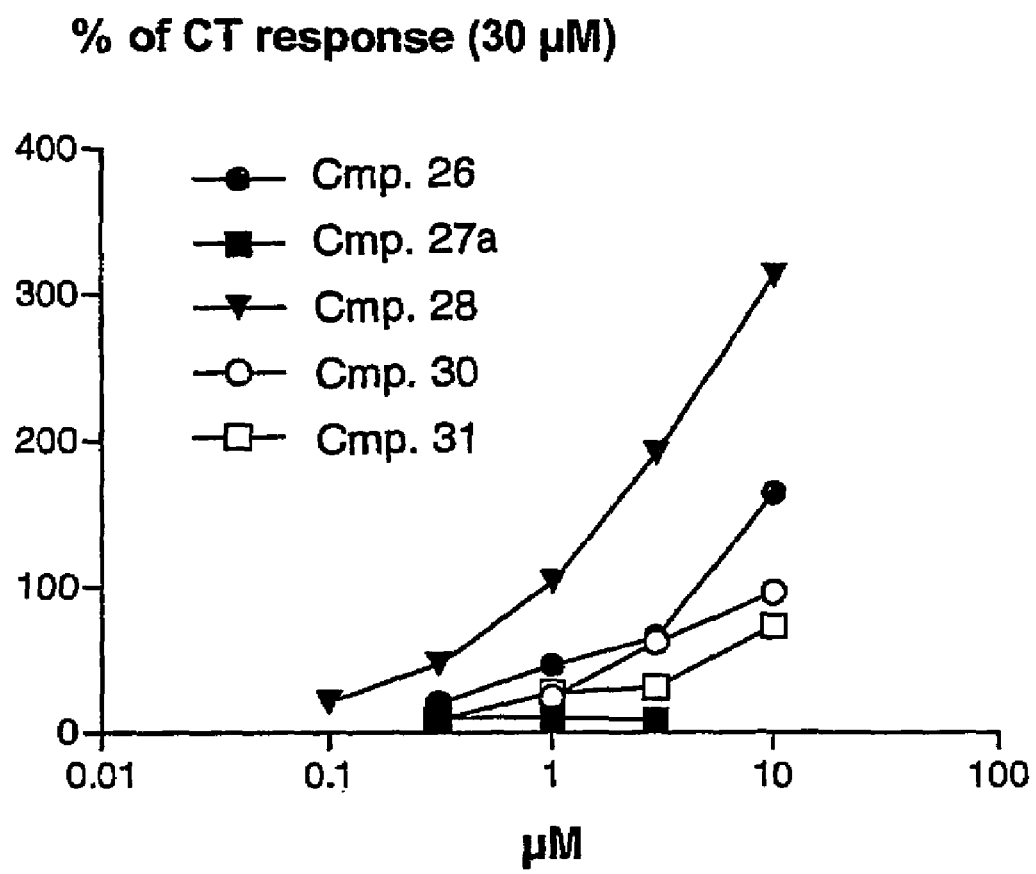
FIG. 1 shows the potentiation of the AMPA response by a test substance (● Cmp. 26; ■ Cmp. 27a; ▼ Cmp. 28; ○ Cmp. 30; □ Cmp. 31) expressed relative to the potentiation of the AMPA response induced by cyclothiazide (CT, 30 μM)
Figure 2:
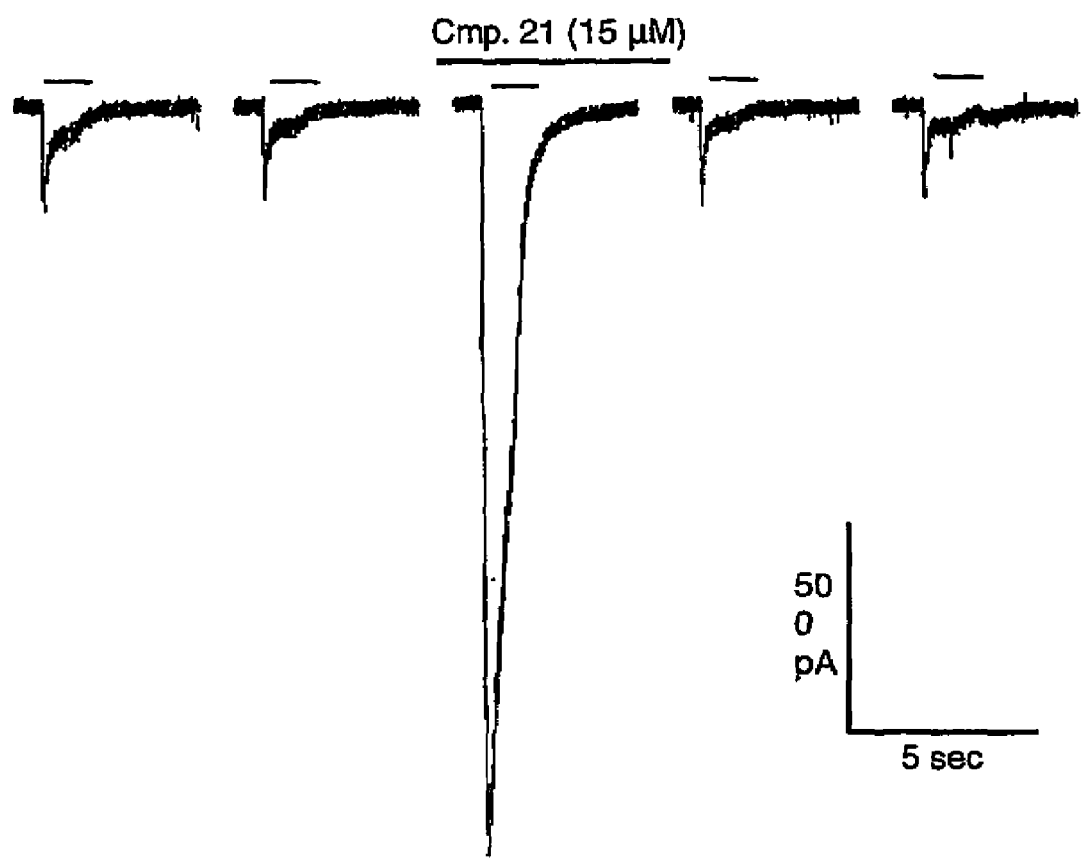
FIG. 2 shows the electrophysiological response of Compound 21 (15 μM)
Figure 3:
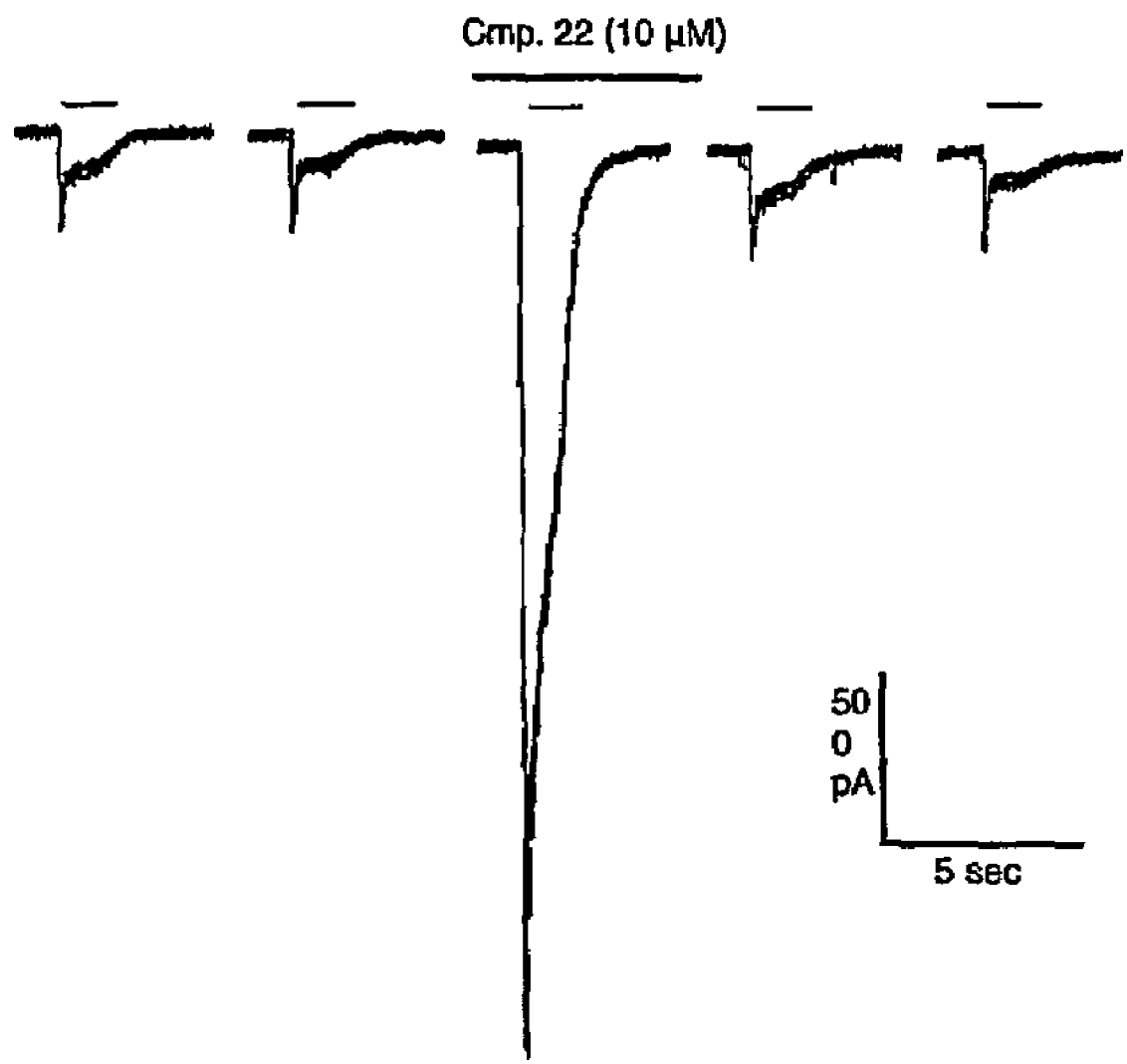
FIG. 3 shows the electrophysiological response of Compound 22 (10 μM)
Figure 4:
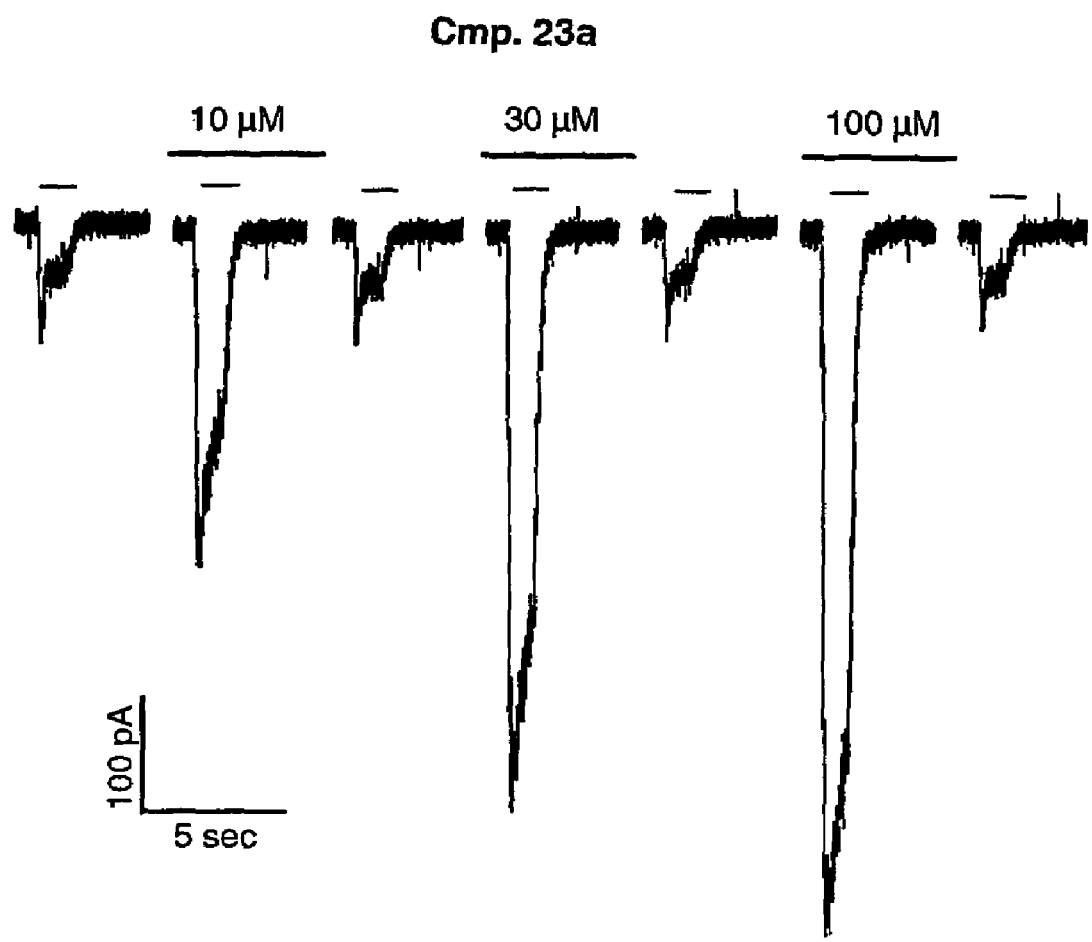
FIG. 4 shows the electrophysiological response of Compound 23a (10, 30 and 100 μM, respectively)
Figure 5:
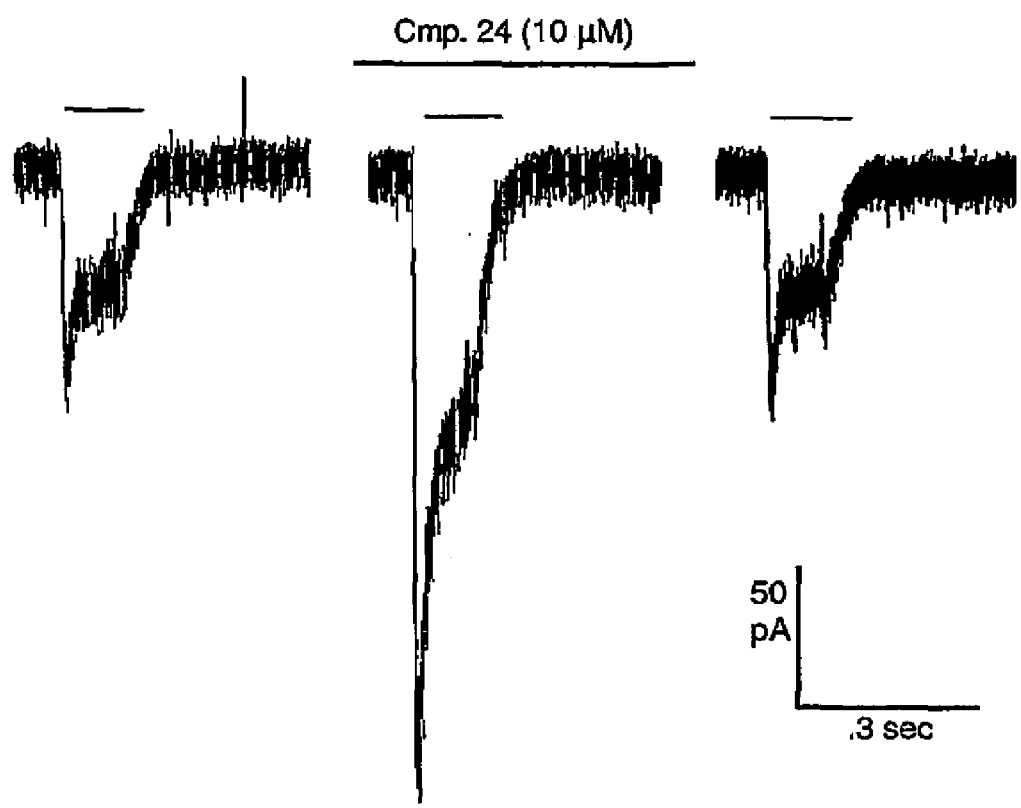
FIG. 5 shows the electrophysiological response of Compound 24 (10 μM)
Figure 6:
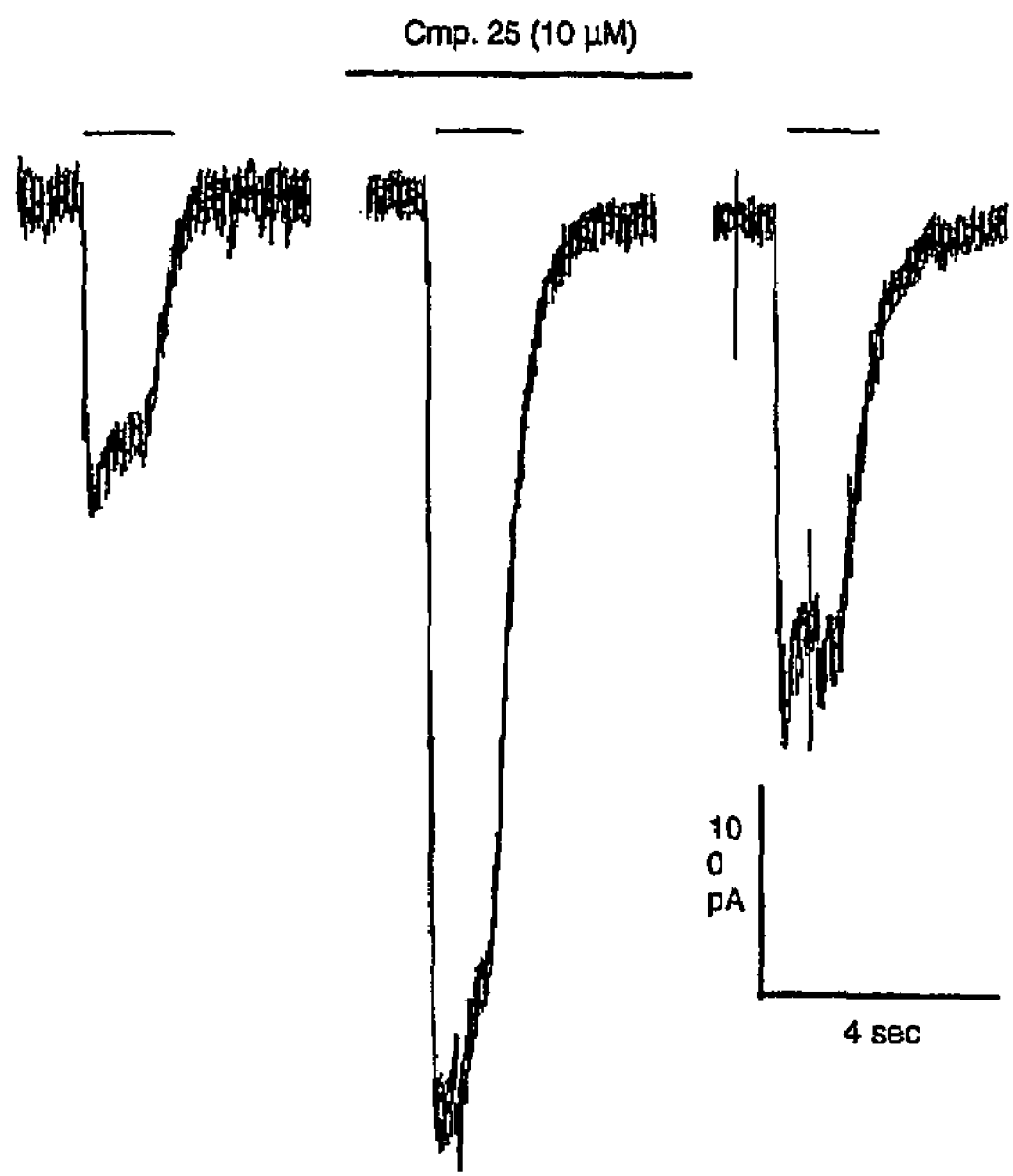
FIG. 6 shows the electrophysiological response of Compound 25 (10 μM)
Figure 7:
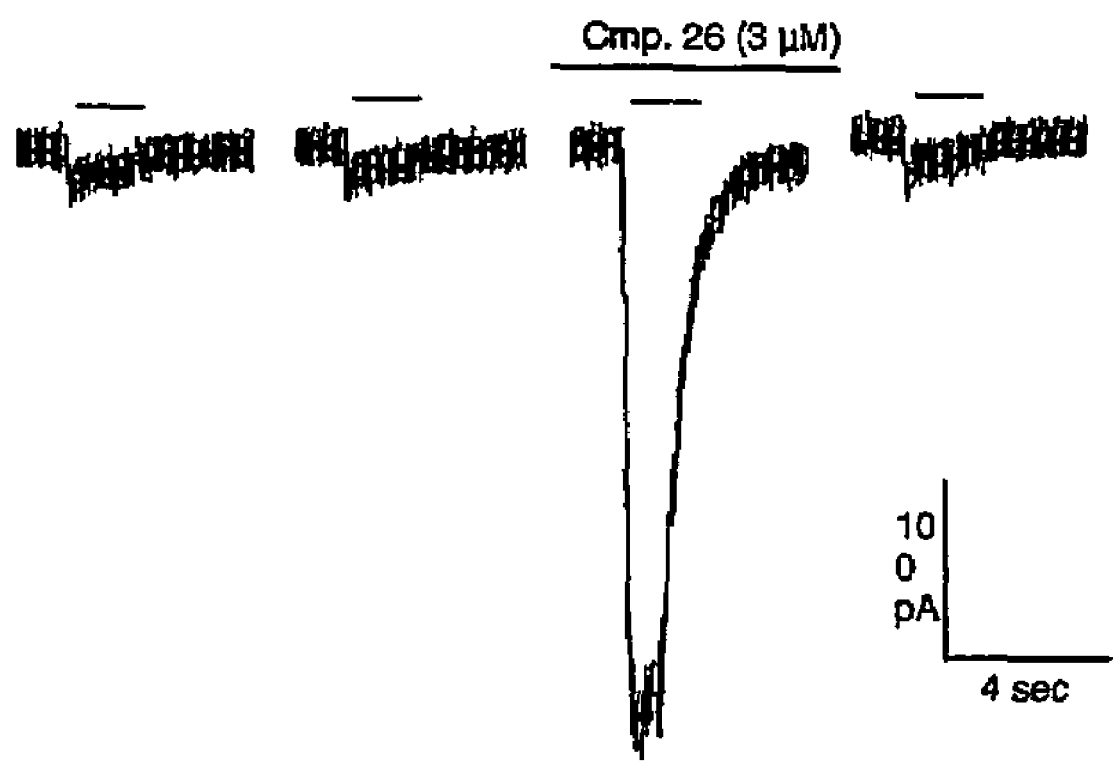
FIG. 7 shows the electrophysiological response of Compound 26 (3 μM)
Figure 8:
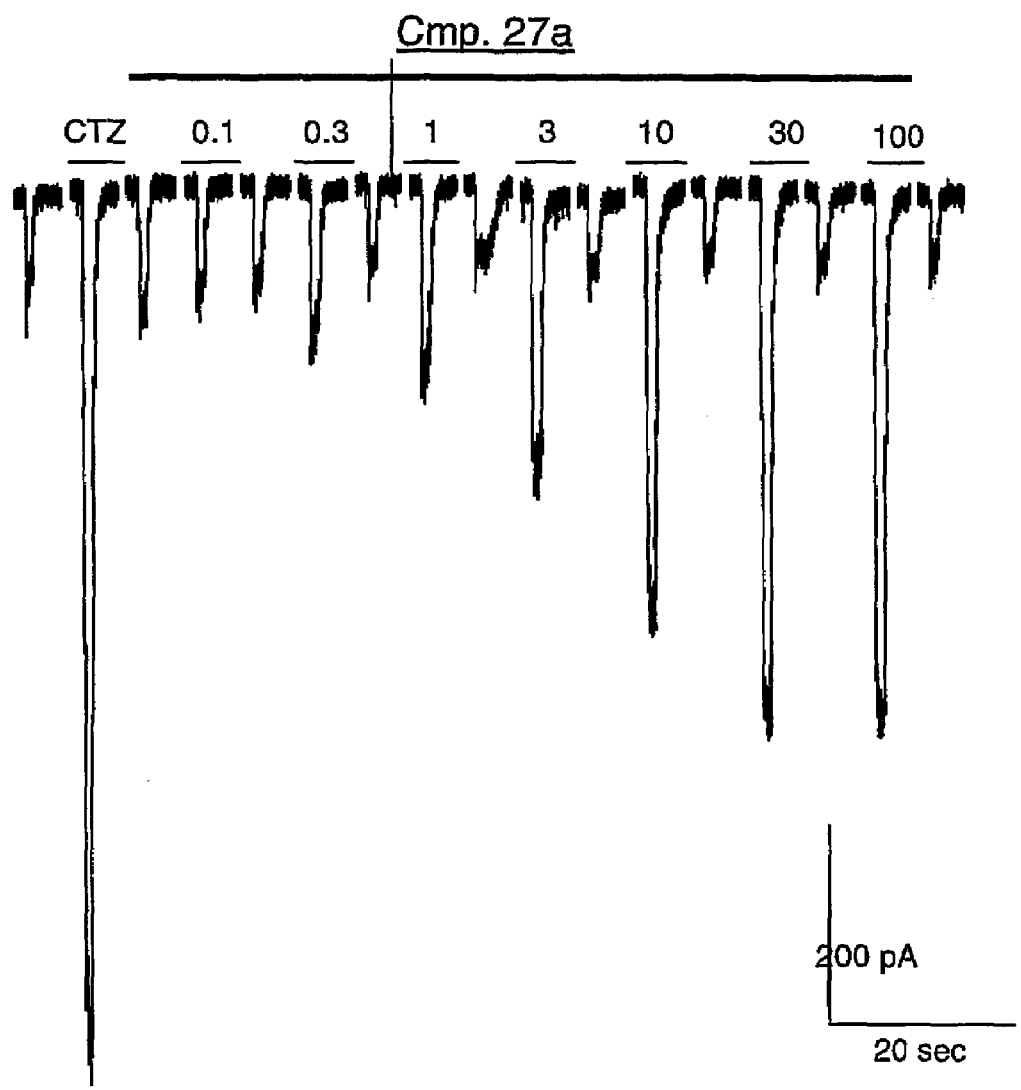
FIG. 8 shows the electrophysiological response of Compound 27a (0.1, 0.3, 1, 3, 10, 30 and 100 μM, respectively).

The invention is further illustrated with reference to the following examples, which are not intended to be in any way limiting to the scope of the invention as claimed.

Example 1

Formation of Building Blocks Type 3:

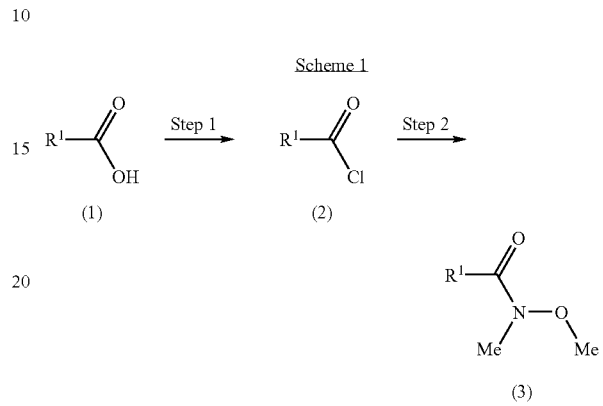

Step 1

A stirred solution of the carboxylic acid 1 (200 mmol), $SOCl_2$ (16 ml, 220 mmol) and DMF (cat. amount) was refluxed for 2 hours. The product 2 was isolated by distillation.

Step 2

A stirred solution of $K_2CO_3$ (36 g, 260 mmol) in water (150 ml) at −5° C. was added MeONHMe, HCl (14.6 g, 150 mmol) and t-butylmethyl ether (150 ml). The acid chloride 2 (200 mmol) was added to the vigorously stirred reaction mixture, such that the internal temperature did not exceed 0° C. The reaction mixture was then allowed to warm up to RT and left with vigorously stirring for 45 minutes. The organic phase was isolated and the aqueous phase extracted with $Et_2O$. The combined organic fractions were dried ($Na_2SO_4$), filtered and evaporated to dryness. The product 3 was purified by distillation to give a yield of generally 65–75%.

Example 2

Formation of Building Blocks Type 7:

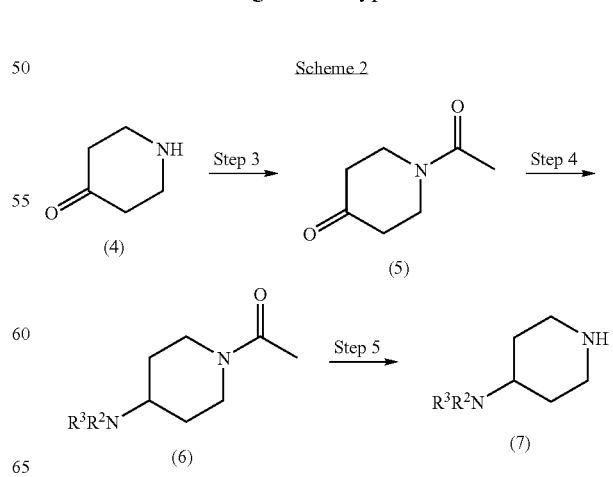

Step 3

A suspension of 4-piperidonium chloride monohydrate (4) (100 g, 650 mmol), Ac$_2$O (237 ml, 3250 mmol) and CHCl$_3$ (300 ml) was refluxed for 60 hours. The reaction mixture was evaporated to dryness, poured onto cold (0° C.) conc. NH$_3$ (aq., 500 ml) and stirred for 1 hour. The aqueous phase was extracted using CH$_2$Cl$_2$ (10×150 ml) and the combined organic fractions dried (MgSO$_4$), filtered and evaporated to dryness to yield 83 g (90%) N-acetyl-4-piperidon (5).

Step 4

An amine or the hydrochloride thereof (1050 mmol) was dissolved in MeOH (200 ml) and pH adjusted to 8.0 using either conc. HCl (aq.) or 10 M NaOH (aq.) respectively. A solution of 5 (24.7 g, 175 mmol) in MeOH (150 ml) was added, followed by NaBH$_3$CN (7.9 g, 125 mmol) and pH adjusted to 8.0. The mixture was left with stirring at RT overnight. A scrubber containing 4 M NaOH (aq.) was connected to the reaction setup and pH of the reaction mixture was carefully adjusted to 1.5 using conc. HCl (aq.). The reaction mixture was stirred for 2 hours, while keeping pH at 1.5. The reaction mixture was evaporated to a thick suspension and then added water (100 ml). The aqueous phase was washed with CH$_2$Cl$_2$ (3×50 ml), pH adjusted to 11 using 10 M NaOH and then extracted using CH$_2$Cl$_2$ (8×125 ml). The combined organic fractions were dried (MgSO$_4$), filtered and evaporated to dryness to yield 6 in 60–70% yield.

Step 5

A stirred mixture of 6 (111 mmol) in water (21 ml) was added conc. HCl (21 ml) dropwise. The mixture was heated to 60° C. overnight, evaporated to dryness, added 99% EtOH and the product, as the dihydrochloride of 7, was isolated by filtration. A general yield of 70–80% was obtained.

Example 3

Formation of Compounds Type 15:

Scheme 3

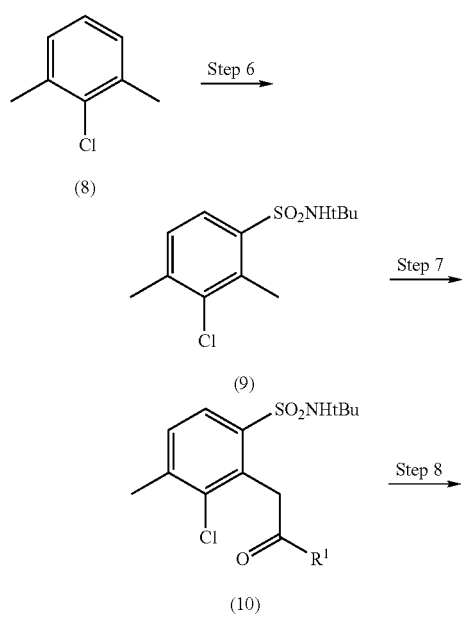

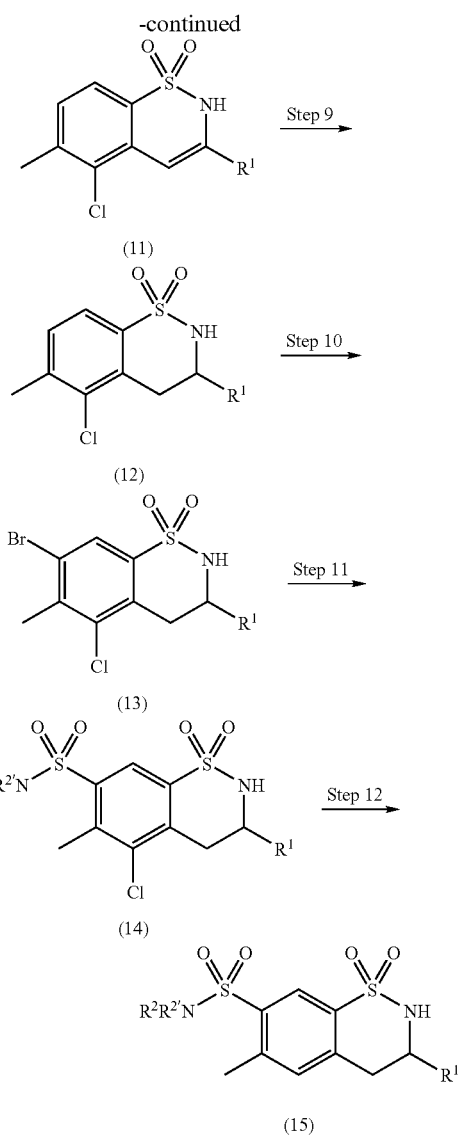

Step 6

A solution of 2-chloro-m-xylene (27 ml, 200 mmol) in CHCl$_3$ (40 ml) at 0° C. was added HSO$_3$Cl (40 ml, 600 mmol) such that the internal temperature did not exceed 5° C. The reaction mixture was allowed to warm up to RT and left with stirring. When the gas evolution ceased, the reaction mixture was stirred for another 2 hours and then carefully poured onto ice. The aqueous phase was extracted using EtOAc (2×100 ml) and the combined organic fractions washed with water (100 ml), dried (Na$_2$SO$_4$), filtered and evaporated to dryness. The oil obtained, was dissolved in t-butylmethyl ether (50 ml) and added to a solution of K$_2$CO$_3$ (50 g), water (200 ml), t-BuNH$_2$ (47 ml, 500 mmol) and t-butylmethyl ether (50 ml). The mixture was stirred vigorously for 1 hours and the organic solvent removed by evaporation. The precipitate formed, was isolated by filtration and recrystallized from MeOH/water to yield 38.1 g (69%) yield of 9.

Step 7

A solution of s-BuLi (1.3 M in cyclohexane, 92 ml, 120 mmol) was slowly added to a solution of 9 (15.2 g, 55 mmol)

and TMEDA (17 ml, 110 mmol) in anhydrous THF (150 ml) at −40° C. The dark red solution was stirred for 40 minutes at −5° C. and then added 3 (60 mmol). The cooling bath was removed and the reaction mixture left with stirring for 2 hours at RT. The reaction was quenched using sat. NH$_4$Cl (aq., 100 ml) and the mixture extracted using EtOAc (3×100 m). The combined organic fractions were washed with 0.5 M HCl (aq., 100 ml), dried (Na$_2$SO$_4$), filtered and evaporated to dryness. The oil obtained, was dissolved in MeOH (150 ml) and heated to reflux. Water was added until the solution became cloudy. The mixture was left for cooling, put on an ice bath, and the product 10 was isolated by filtration. A general yield of 60–70% was obtained.

Step 8

A solution of 10 (82 mmol) in trifluroacetic acid (80 ml) was stirred at RT for 2 hours. The reaction mixture was added water (500 ml) and the product 11 isolated by filtration in quantitative yield.

Step 9

A solution of 11 (50 mmol) in trifluoroacetic acid (100 ml) was added Et$_3$SiH (9.6 ml, 60 mmol) and the mixture was left with stirring for 1 hour at RT. The reaction mixture was evaporated to dryness, added 10% Na$_2$CO$_3$ (aq., 50 ml) and extracted using EtOAc (3×150 ml). The combined organic fractions were dried (Na$_2$SO$_4$), filtered and evaporated to dryness. The oil obtained, was dissolved in a minimum of MeOH and heated to reflux. Water was added until the solution became cloudy. The mixture was left for cooling, put on an ice bath and the product 12 was isolated by filtration. A general yield of 80–90% was obtained.

Steps 8, 9

Step 8 and 9 may also be performed as a one-pot reaction.

Step 10

A stirred solution of 12 (20 mmol) in trifluroacetic acid (15 ml) and H$_2$SO$_4$ (1.5 ml) was added NBS (3.6 g, 20 mmol) in small portions over 1 hour. The reaction mixture was stirred for 3.5 hours and then added small portions of NBS (overall 4.8 g, 26.8 mmol was added) until GCMS indicated complete transformation of 12. The reaction mixture was poured into water, and the crude product isolated by filtration. The crude product was recrystallized from MeOH (100 ml) to yield 13 in a general yield of 65–75%.

Steps 8, 9, 10

Step 8, 9 and 10 may also be performed as a one-pot reaction.

Step 11

A solution of n-BuLi (2.5 M in hexanes, 11.2 ml, 28 mmol) was slowly added to a stirred solution of 13 (13.2 mmol) in anhydrous THF (100 ml) at −78° C., such that the internal temperature did not exceed −65° C. The reaction mixture was stirred at −78° C. for 15 minutes, and then slowly added a sat. solution of SO$_2$ (g) in anhydrous THF (25 ml). Alternatively, SO$_2$ (g) was bobbled through the reaction mixture. The reaction mixture was stirred at −78° C. for 30 minutes, and then added SO$_2$Cl$_2$ (2.25 ml, 28 mmol). The cooling bath was removed, and the reaction mixture allowed to warm up and left with stirring at RT for 1.5 hours. The reaction mixture was poured into a solution of K$_2$CO$_3$ (50 g), water (200 ml), t-butylmethyl ether (50 ml) and the appropriate amine (100 mmol). The mixture was stirred vigorously for 1.5 hours and the organic solvent removed by evaporation. The precipitate formed, was filtered off, washed with water, and and reprecipitated from MeCN/water to yield 14 in a general yield of 30–50%.

Step 12

A suspension of 14 (4.2 mmol) and 10% Pd/C (cat.) in 96% EtOH (200 ml) and THF (50 ml) was hydrogenated at 1 atm. for 18 hours. The reaction mixture was filtered through celite and the filtrate evaporated to dryness. The crude product was reprecipitated from MeCN/water to yield 15 in 75–90% yield.

Formation of Salts

When product 15 contained an aliphatic amine moiety, the hydrochloride was prepared by gently heating a solution of 15 (2.2 mmol) in 3 M HCl in 99% EtOH (20 ml). The mixture was cooled to RT, put on ice, and the hydrochloride of 15, isolated by filtration. A general yield of 75–90% was obtained.

Example 4

Formation of Compounds Type 20:

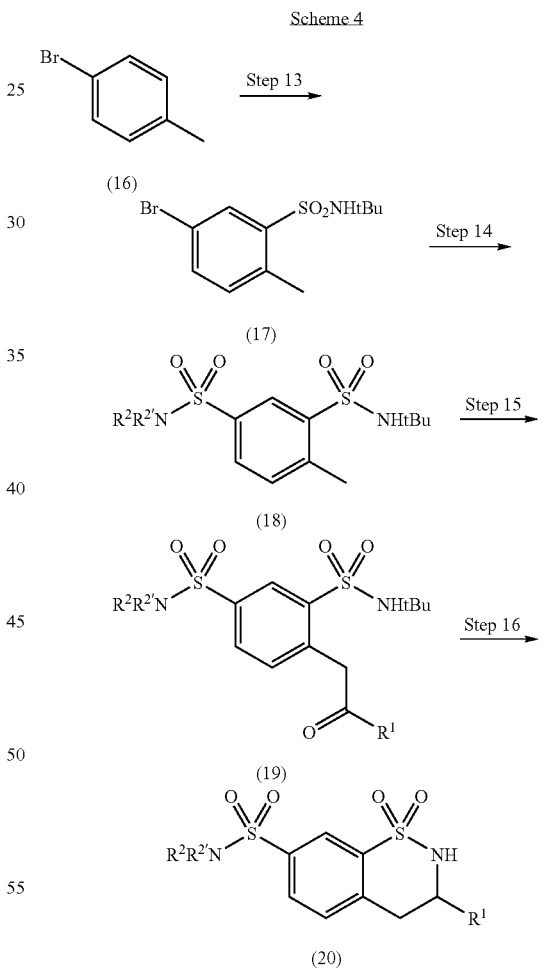

Step 13

A solution of 4bromotoluene (16) (102 g, 600 mmol) in CHCl$_3$ (250 ml) at 0° C. was added HSO$_3$Cl (134 ml, 2000 mmol) such that the internal temperature did not exceed 5° C. The reaction mixture was allowed to warm up to RT and left with stirring. When the gas evolution ceased, the reaction mixture was stirred for another 2 hours and then carefully poured onto ice (300 g). The organic phase was isolated, and the aqueous phase was extracted using CH$_2$Cl$_2$ (2×250 ml). The combined organic fractions were washed with water (100 ml), dried (Na$_2$SO$_4$), filtered and evaporated to dryness. The oil obtained, was dissolved in THF (150 ml) and added to a solution of K$_2$CO$_3$ (138 g), water (300 ml), t-BuNH$_2$ (86 ml, 800 mmol) and THF (150 ml). The mixture was stirred vigorously over night, and the organic solvent removed by evaporation. The precipitate formed, was isolated by filtration and washed with water to yield 99.8 g (54%) of 17.

Step 14

A solution of n-BuLi (2.5 M in hexanes, 19 ml, 47.5 mmol) was slowly added to a stirred solution of 17 (20 mmol) in anhydrous THF (100 ml) at −78° C., such that the internal temperature did not exceed −70° C. The reaction mixture was stirred at −78° C. for 20 minutes. The reaction was quenched with SO$_2$ (g), which was bobbled through the reaction mixture. The reaction mixture was stirred at −78° C. for 30 minutes, and then added SO$_2$Cl$_2$ (3.3 ml, 40 mmol). The cooling bath was removed, and the reaction mixture allowed to warm up and left with stirring at RT for 1.5 hours. The reaction mixture was poured into a solution of the appropriate amine (300 mmol) in anhydrous THF (150 ml) to yield a yellow suspension. The suspension was stirred for 1 hour at RT, and the volume reduced to half size by evaporation. The suspension was added water (100 ml) and 4 M, HCl (30 ml) and then extracted using EtOAc (4×100 mL). The combined organic fractions were washed with NaHCO$_3$ (100 ml), dried (Na$_2$SO$_4$), filtered and evaporated to dryness. The isolated oil was precipitated from MeOH/water to yield 18 in 30–50% yield as a white solid.

Step 14

Alternatively, to pouring the reaction mixture into a solution of the appropriate amine, the reaction of the sulfonylchloride into the sulfonamide may be conducted similarly to the method described for step 11, ie. using K$_2$CO$_3$, water, t-butylmethyl ether and the appropriate amine.

Step 15

A solution of s-BuLi (1.3 M in cyclohexane, 16.6 ml, 21.5 mmol) was slowly added to a solution of 18 (3.6 g, 10.8 mmol) and TMEDA (3.3 ml, 21.6 mmol) in anhydrous THF (36 ml) at −25° C. The solution was stirred for 1 hour at −10° C. and then added 3 (12.6 mmol). The cooling bath was removed and the reaction mixture left with stirring for 2 hours at RT. The reaction was quenched by addition of sat. NH$_4$Cl (aq., 10 ml) and water (10 ml), and the mixture extracted using EtOAc (3×60 ml). The combined organic fractions were washed with sat. NaHCO$_3$ (aq., 50 ml), dried (Na$_2$SO$_4$), filtered and evaporated to dryness to yield the product 19 in 70–90% yield.

Step 16

A solution of 19 (10.7 mmol) in trifluoroacetic acid (33 ml) was stirred at RT over night. The reaction mixture was added Et$_3$SiH (1.72 ml, 10.7 mmol) and stirred for another 1 hour. The reaction mixture was added 10% Na$_2$CO$_3$ (aq., 65 ml) and water (150 ml), and the precipitate formed, was isolated by filtration. The crude product was reprecipitated from MeCN/water to yield 20 in a general yield of 30–60%.

Formation of Salts

When product 20 contained an aliphatic amine moiety, the hydrochloride was prepared by gently heating a solution of 20 in a minimum of 3 M HCl in 99% EtOH. The mixture was cooled to RT, put on ice and the hydrochloride of 20, isolated by filtration. A general yield of 70–90% was obtained.

Example 5

(3RS)-3-Cyclohexyl-7-(piperidine-1-sulfonyl)-3,4-dihydro-2H-benzo[e][1,2]thiazine-1,1-dioxide (Compound 21)

Using the general method the title compound was obtained.

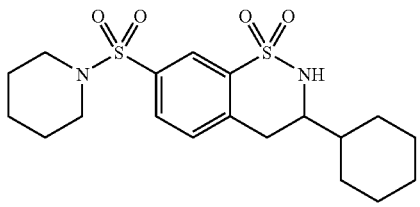

M.p.: 200–201° C.
MS (FAB+): 413 (M + 1)

Example 6

(3RS)-3-Cyclopentyl-7-(piperidine-1-sulfonyl)-3,4-dihydro-2H-benzo[e][1,2]thiazine-1,1-dioxide (Compound 22)

Using the general method the title compound was obtained.

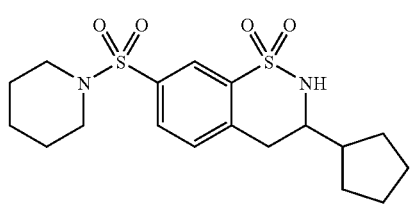

M.p.: 211–213° C.
MS (FAB+): 399 (M + 1)

Example 7a (3RS)-3-Cyclopentyl-7-(4-methyl-piperazine-1-sulfonyl)-3,4-dihydro-2H-benzo[e][1,2]thiazine-1,1-dioxide (Compound 23a)

Using the general method the title compound was obtained.

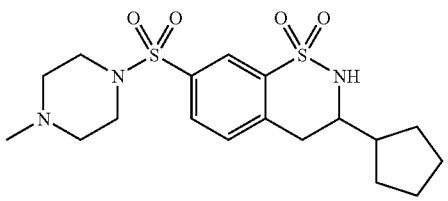

M.p.: 223–225° C.
MS (FAB+): 414 (M + 1)

Example 7b (3RS)-3-Cyclopentyl-7-(4-methyl-piperazine-1-sulfonyl)-3,4-dihydro-2H-benzo[e][1,2]thiazine-1,1-dioxide, hydrochloride (Compound 23b)

Using the general method the title compound was obtained.
M.p.: 234–236° C.

Example 8

(3RS)-3-Cyclohexyl-7-(4-methyl-piperazine-1-sulfonyl)-3,4-dihydro-2H-benzo[e][1,2]thiazine-1,1-dioxide (Compound 24)

Using the general method the title compound was obtained.

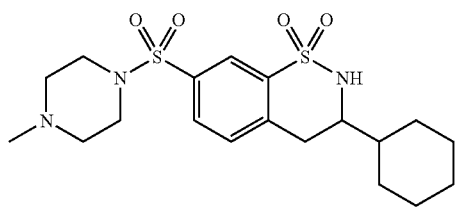

M.p.: 221–224° C.
MS (FAB+): 428 (M + 1)

Example 9

(3RS)-3-Cyclopentyl-6-methyl-7-(piperidine-1-sulfonyl)-3,4-dihydro-2H-benzo[e][1,2]thiazine-1,1-dioxide (Compound 25)

Using the general method the title compound was obtained.

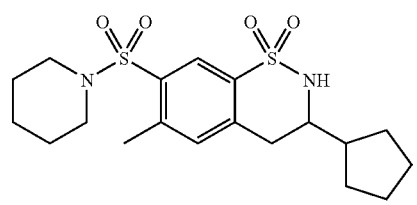

M.p.: 178–180° C.
MS (FAB+): 413 (M + 1)

Example 10

(3RS)-3-Cyclopentyl-6-methyl-7-(morpholine-4-sulfonyl)-3,4-dihydro-2H-benzo[e][1,2]thiazine-1,1-dioxide (Compound 26)

Using the general method the title compound was obtained.

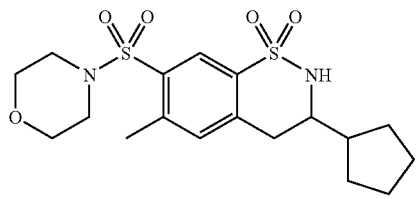

M.p.: 213–216° C.
MS (FAB+): 415 (M + 1)

Example 11a (3RS)-3-Cyclopentyl-6-methyl-7-(4-methyl-piperazine-1-sulfonyl)-3,4-dihydro-2H-benzo[e][1,2]thiazine-1,1-dioxide (Compound 27a)

Using the general method the title compound was obtained.

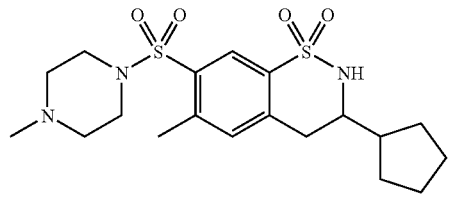

M.p.: 101–103° C.
MS (FAB+): 428 (M + 1)

Example 11b (3RS)-3-Cyclopentyl-6-methyl-7-(4-methyl-piperazine-1-sulfonyl)-3,4-dihydro-2H-benzo[e][1,2]thiazine-1,1-dioxide, hydrochloride (Compound 27b)

Using the general method the title compound was obtained.
M.p.: 251° C. (dec.)

Example 12

(3RS)-3-Cyclopentyl-6-methyl-7-(N,N-dimethylamine-1-sulfonyl)-3,4-dihydro-2H-benzo[e][1,2]thiazine-1,1-dioxide (Compound 28)

Using the general method the title compound was obtained.

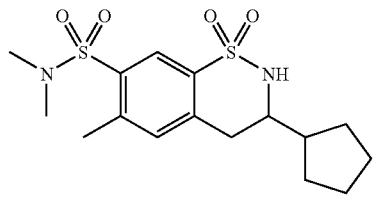

M.p.: 182–185° C.
MS (FAB+): 373 (M + 1)

Example 13

(3RS)-3-Cyclopentyl-6-methyl-7-(4-hydroxypiperidine-1-sulfonyl)-3,4-dihydro-2H-benzo[e][1,2]thiazine-1,1-dioxide (Compound 29)

Using the general method the title compound was obtained.

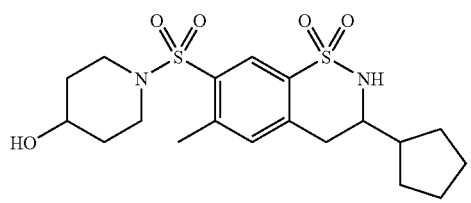

M.p.: 120–140° C.
MS (FAB+): 429 (M + 1)

Example 14

(3RS)-3-Cyclopentyl-7-(N,N-dimethylamine-1-sulfonyl)-3,4-dihydro-2H-benzo[e][1,2]thiazine-1,1-dioxide (Compound 30)

Using the general method the title compound was obtained.

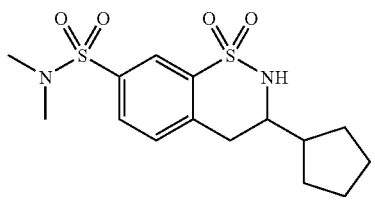

M.p.: 203° C.
MS (FAB+): 359 (M + 1)

Example 15

(3RS)-3-Cyclopentyl-7-(morpholine-4-sulfonyl)-3,4-dihydro-2H-benzo[e][1,2]thiazine-1,1-dioxide (Compound 31)

Using the general method the title compound was obtained.

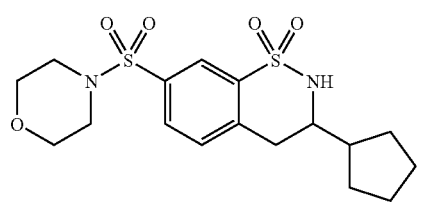

M.p.: 186–196° C.
MS (FAB+): 401 (M + 1)

Example 16

[1-(3-Cyclopentyl-1,1-dioxo-1,2,3,4-tetrahydro-1$\lambda^6$-benzo[e][1,2]thiazine-7-sulfonyl)-piperidin-4-yl]-dimethyl-amine (Compound 32)

Using the general method the title compound was obtained.

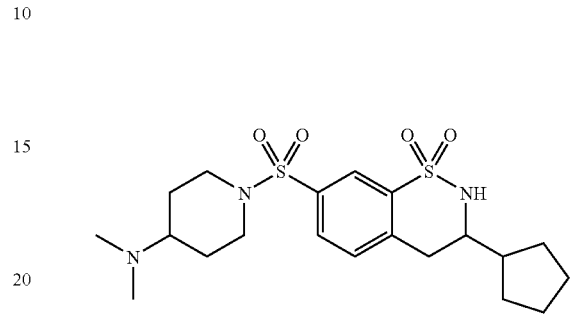

Example 17

Spirocyclic Compounds (Compounds 33a–l)

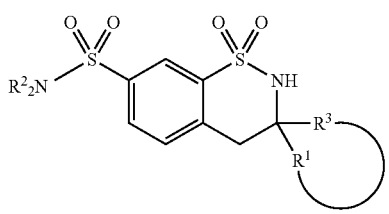

(33)

Compounds of type 33, wherein a spirocyclic ring is present, is prepared using a cyclic ketone in Step 7 (Scheme 3) or Step 15 (Scheme 4). The thus generated intermediary alcohol is ring closed to yield compounds type 33 by treatment with acid such as $H_2SO_4$, by use of other dehydrating conditions such as e.g. Mitsunobu conditions, or by use of $P_2O_5$ or polyphosphoric acid. Alternatively, the ring closure is performed transforming the alcohol into the chloride, bromide or tosylate by treatment with $SO_2Cl_2$, $SO_2Br_2$ (or $Ph_3P/Br_2$, $NEt_3$) or TsCl, respectively, followed by heating, e.g. in the presence of a base like triethylamine.

Using this method the following compounds are prepared:

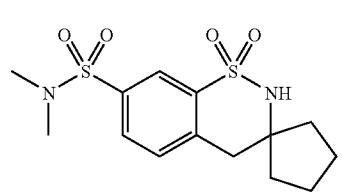

(33a)

-continued

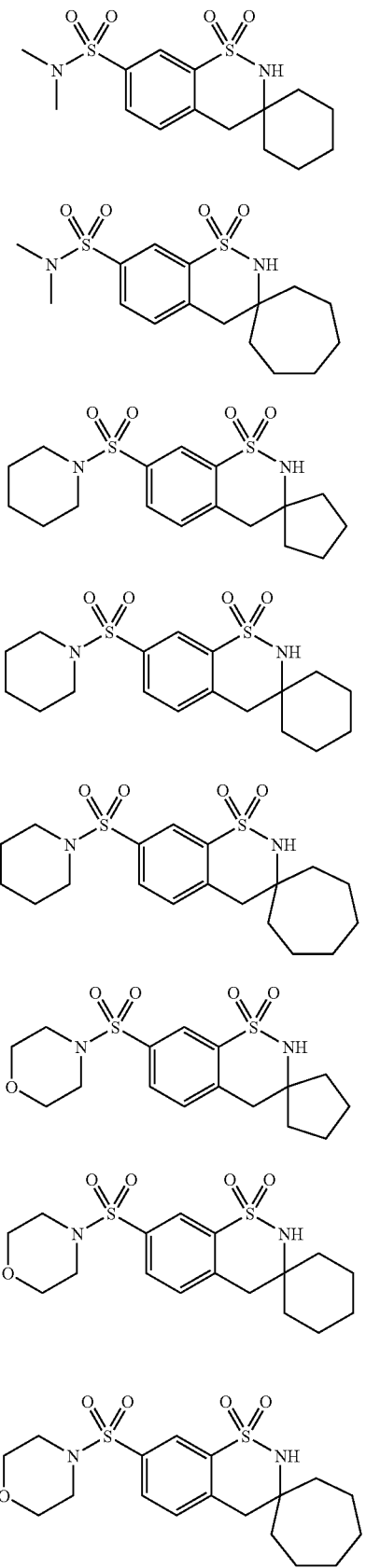

(33b)
(33c)
(33d)
(33e)
(33f)
(33g)
(33h)
(33i)

-continued

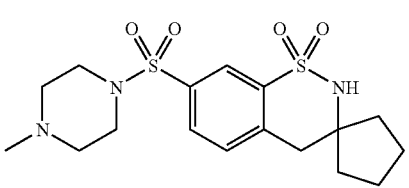

(33j)

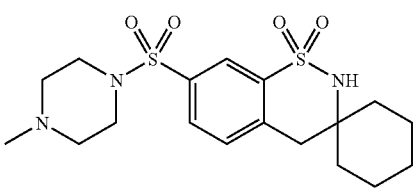

(33k)

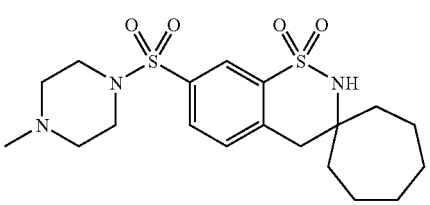

(33l)

Example 18

AMPA Induced GABA Release

In this example the potentiation of AMPA induced [$^3$H] GABA release from cultured cortical neurons was examined.

[$^3$H]GABA Release: Cerebral cortices of 15–16 day-old NMRI mouse embryos are chopped in 0.4×0.4 mm cubes and the tissue is dissociated by mild trypsinization (0.1% (wt/vol) trypsin, 37° C., 10 minutes). Subsequently the cell suspension (3 mill/ml) is inoculated into poly-L-lysine-coated 30 mm Petri dishes (3 ml/dish) containing a slightly modified DMEM (24.5 mM KCl) supplemented with p-aminobenzoate (7 μM), insulin (100 mU/L) and 10% (vol/vol) horse serum. Cells are maintained in culture for 5–7 days with the addition of the antimitotic agent cytosine arbinoside (5 μM) from day 2 in vitro to prevent glial proliferation.

Release experiments are performed using the model described by Drejer et al. (Drejer et al. *Life Sci.* 1986 38 2077). Cerebral cortex neurons cultured in Petri dishes (30 mm) are added 100 mM γ-vinyl-GABA one hour before the experiment in order to inhibit degradation of GABA in the neurons. 30 min before the experiment 5 μCi $^3$H-GABA is added to each culture. After this preloading period the cell monolayer at the bottom of the dish is covered with a piece of nylon mesh to protect the cells against mechanical damage and to facilitate dispersion of medium over the cell layer. The preloading medium is removed and the Petri dishes are placed in a superfusion system consisting of a peristaltic pump continuously delivering thermostated 37° C. superfusion medium (HEPES buffered saline (HBS): 10 mM HEPES, 135 mM NaCl, 5 mM KCl, 0.6 mM MgSO$_4$, 1.0 mM CaCl$_2$ and 6 mM D-glucose; pH 7.4) from a reservoir to the top of the slightly tilted Petri dish. The medium is continuously collected from the lower part of the dish and delivered to a fraction collector. Initially, the cells are superfused with HBS for 30 min (flow rate 2 ml/min). Then cells are stimulated for 30 sec every 4 min by changing the superfusion medium from HBS to a corresponding medium containing 5 μM AMPA in the absence or presence of modulators. The induced release of $^3$H-GABA (cpm) is corrected for the mean basal release (cpm) before and after the stimulation and used for calculation of the test value.

The results of these experiments are presented in FIG. 1.

The potentiation of the AMPA response by a test substance is expressed relative to the potentiation of the AMPA response induced by cyclothiazide (30 μM).

Example 19

Electrophysiological Patch Clamp Experiments

Experiments were performed in voltage clamp using conventional whole cell patch clamp methods (see Hamill O P, Marty A, Neher E, Sakmann B & Sigworth F J: Improved patch-clamp techniques for high-resolution current recording from cells and cell-free membrane patches; *Pflügers Arch.* 1981 39 85–100), essentially as described Mathiesen et al. (Mathiesen C, Varming T & Jensen L H: In vivo and in vitro evaluation of AMPA receptor antagonists in rat hippocampal neurones and cultured mouse cortical neurons; *Eur. J. Pharmacol.* 1998 353 159–167).

The following salt solutions were used (mM): NaCl (140), KCl (4), CaCl$_2$ (2), MgCl$_2$ (1), Sucrose (30; Available from Fluka Chemie, Buchs, Switzerland), Tetrodotoxin (0.0003; Available from Alomone Labs, Jerusalem, Israel), Bicuculline Methiodide (0.005; Available from RBI, MA, USA) and HEPES (10, pH 7.4).

Intracellular solution (mM): CsCl (120), CsF (20), MgCl$_2$ (2), EGTA (10), ATP (4), HEPES (10, pH=7.2).

Cell cultures: Mouse neocortical neurons were cultured essentially as described by Drejer et al. (Drejer J, Honoré T & Schousboe A: Excitatory amino acid-induced release of $^3$H-GABA from cultured mouse cerebral cortex interneurons; *J. Neurosci.* 1987 7 2910–2916).

Briefly, the forebrains from embryonic (E17) NMRI mice were removed under sterile conditions. Pregnant (9 days) NMRI mice were obtained from Bomholtgaard Breeding and Research Center, Ry, Denmark. The tissue was chopped in 0.4 mm cubes and the triturated with trypsin (12.5 μg/ml) and DNAse (2.5 μg/ml), 15 minutes, 37° C. The cells were suspended at a concentration of 1×10$^6$ cells/ml in a slightly modified DMEM containing horse serum (10% (v/v)), penicillin (333 U/ml), paraaminobenzoic acid (1 μg/ml), L-glutamine (0.5 mM), insulin (0.08 U/ml) and KCl (23.8 mM). Horse serum, N$_2$ supplement and culture media were purchased from Life Technologies (GIBCO), Roskilde, Denmark.

The cell suspension was subsequently inoculated into poly-L-lysine coated 35 mm Petri dishes (2 ml/dish). Glass coverslips (3.5 mm) were placed in the dishes before coating. After 24 hours in culture, the medium was replaced by freshly made medium containing 1% N$_2$ supplement instead of serum.

The cells were kept in culture for 7–14 days at 37° C. (5% CO$_2$/95% O$_2$) before experiments were carried out.

Electronics, programs and data acquisition: The amplifier used was the EPC-9 (HEKA-electronics, Lambrect, Germany) run by a Power Macintosh G3 computer via an ITC-16 interface. Experimental conditions were set with the Pulse-software accompanying the amplifier. Data were low pass filtered and sampled directly to hard-disk at a rate of 3 times the cut-off frequency.

Pipettes and electrodes: Pipettes were pulled from borosilicate glass (Modulohm, Copenhagen, Denmark) using a horizontal electrode puller (Zeitz-Instrumente, Augsburg, Germany). The pipette resistances were 1.7–2.4 MΩ in the salt solutions used in these experiments. The pipette electrode was a chloridized silver wire, and the reference was a silverchloride pellet electrode (In Vivo Metric, Healdsburg, USA) fixed to the experimental chamber. The electrodes were zeroed with the open pipette in the bath just prior to sealing.

Experimental procedure: Coverslips were transferred to a 15 μl experimental chamber mounted on the stage of an inverted microscope (IMT-2, Olympus) supplied with Nomarski optics. The neurons were continuously superfused with extracellular saline at a rate of 2.5 ml/min. After giga-seal formation (1–5 GΩ, success-rate≈90%) the whole cell configuration was attained by suction.

The cells were held at a holding voltage of −60 mV, and at the start of each experiment the current was continuously measured for at least 30 seconds to ensure a stable leak current.

AMPA-containing solutions were delivered to the chamber through a custom-made gravity-driven flowpipe, the tip of which was placed approximately 50 μm from the cell. Application was triggered when the tubing connected to the flow pipe were compressed by a valve controlled by the Pulse-software. AMPA (30 μM) was applied for 1 second every 45 seconds.

After obtainment of responses of repeatable amplitude, the compound to be tested was included in both the chamber and in the AMPA-containing solution. The compound was present until responses of a new repeatable was obtained.

The sample interval in all experiments was 310 μsecond.

All experiments were performed at room temperature (20–25° C.).

Unless otherwise specified, the reagents are from Sigma, USA.

Results

The results of these experiments are presented in FIGS. 2–8 below. Compound 21, Compound 22, Compound 23a, Compound 24, Compound 25, Compound 26 and Compound 27a all potentiate the current induced by application of 30 μM AMPA (thin horizontal lines).

It is seen that the potentiation in every case is reversible. The effect of the compounds is concentration-dependent, as exemplified for Compound 23a and Compound 27a. In the experiment with Compound 27a, the effect was compared to the effect of 100 μM Cyclothiazide. In all experiments, the time between AMPA stimulations was 45 seconds.

The invention claimed is:

1. A benzothiazine derivative of Formula I (I)

any of its enantiomers or any mixture of its enantiomers, or a pharmaceutically acceptable salt thereof, wherein $R^1$ represents hydrogen, alkyl, alkenyl, alkynyl, cycloalkyl, cycloalkenyl, aryl or heteroaryl; and one of $R^2$ and $R^3$ represents hydrogen or alkyl other than t-butyl while the other of $R^2$ and $R^3$ represents cycloalkyl or cycloalkenyl; and R⁴ and R⁵, independently of each another, represent hydrogen, alkyl, alkenyl, alkynyl, cycloalkyl, cycloalkenyl, and/or a saturated or partially saturated mono- or bi-cyclic heterocyclic ring; and R⁶ represents hydrogen, halogen, alkyl, cycloalkyl, haloalkyl or alkoxy; and R⁷ represents hydrogen, alkyl, cycloalkyl, hydroxyalkyl, alkenyl, alkynyl or halogen, or a group of the formula —R¹⁰—NR⁹R⁸, —R¹⁰—NO₂, —R¹⁰—OR⁸, —R¹⁰—SR⁸, —R¹⁰—S(=O)NR⁹R⁸, —R¹⁰—S(=O)R⁸, —R¹⁰—S(=O)₂R⁸, —R¹⁰—S(=O)₂OR⁸, —R¹⁰—S(=O)₂NR⁹R⁸, —R¹⁰—NR⁹S(=O)₂R⁸, —R¹⁰—NR¹¹S(=O)₂NR⁹R⁸, —R¹⁰—CN, —R¹⁰—C(=NR⁹)R⁸, —R¹⁰—C(=NNR⁹)R⁸, —R¹⁰—C(=NOR⁹)R⁸, —R¹⁰—C(=O)R⁸, —R¹⁰—C(=O)NR⁹R⁸, —R¹⁰—C(=S)R⁸, —R¹⁰—C(=O)OR⁸, —R¹⁰—C(=S)OR⁸, —R¹⁰—C(=O)SR⁸, —R¹⁰—C(=S)SR⁸, —R¹⁰—C(=O)NR⁹(OR⁸), —R¹⁰—C(=S)NR⁹(OR⁸), —R¹⁰—C(=O)NR⁹(SR⁸), —R¹⁰—C(=S)NR⁹(SR⁸), —R¹⁰—CH(CN)₂, —R¹⁰—C(=O)NR⁹R⁸, —R¹⁰—NR⁹C(=O)R⁸, —R¹⁰—NR¹¹C(=O)NR⁹R⁸, —R¹⁰—C(=S)NR⁹R⁸, —R¹⁰—CH[C(=O)R⁸]₂, —R¹⁰—CH[C(=S)R⁸]₂, —R¹⁰—CH[C(=O)OR⁸]₂, —R¹⁰—CH[C(=S)OR⁸]₂, —R¹⁰—CH[C(=O)SR⁸]₂, —R¹⁰—CH[C(=S)SR⁸]₂, or —R¹⁰—CH[C(=S)NR⁹R⁸]₂; wherein R⁸, R⁹ and R¹¹, independently of each another, represent hydrogen, alkyl, alkenyl, alkynyl, cycloalkyl, alkoxy, hydroxy, aryl or heteroaryl, which aryl or heteroaryl may optionally be substituted one or more times with alkyl, cycloalkyl, alkoxy, halogen, hydroxy, amino, trifluoromethyl, trifluoromethoxy or nitro; or R⁸ and R⁹, together with the atoms to which they are bound, form a heterocyclic ring, which heterocyclic ring may optionally be substituted one or more times with alkyl, cycloalkyl, alkoxy, halogen, hydroxy, amino, trifluoromethyl, trifluoromethoxy or nitro, and R¹¹ is as defined above; and R¹⁰ is absent or represents a linker selected from alkyl, alkenyl, alkynyl, cycloalkyl, aryl or heteroaryl; or R⁷ represents a mono- or polycyclic carbocyclic or heterocyclic group, which carbocyclic or heterocyclic group may optionally be substituted one or more times with substituents selected from alkyl, cycloalkyl, hydroxyalkyl, alkenyl, alkynyl or halogen, or a group of the formula —R¹⁰—NR⁹R⁸, —R¹⁰—NO₂, —R¹⁰—OR⁸, —R¹⁰—SR⁸, —R¹⁰—S(=O)NR⁹R⁸, —R¹⁰—S(=O)R⁸, —R¹⁰—S(=O)₂R⁸, —R¹⁰—S(=O)₂OR⁸, —R¹⁰—S(=O)₂NR⁹R⁸, —R¹⁰—NR⁹S(=O)₂R⁸, —R¹⁰—NR¹¹S(=O)₂NR⁹R⁸, —R¹⁰—CN, —R¹⁰—C(=NR⁹)R⁸, —R¹⁰—C(=NNR⁹)R⁸, —R¹⁰—C(=NOR⁹)R⁸, —R¹⁰—C(=O)R⁸, —R¹⁰—C(=O)NR⁹R⁸, —R¹⁰—C(=S)R⁸, —R¹⁰—C(=O)OR⁸, —R¹⁰—C(=S)OR⁸, —R¹⁰—C(=O)SR⁸, —R¹⁰—C(=S)SR⁸, —R¹⁰ C(=O)NR⁹(OR⁸), —R¹⁰—C(=S)NR⁹(OR⁸), —R¹⁰—C(=O)NR⁹(SR⁸), —R¹⁰—C(=S)NR⁹(SR⁸), —R¹⁰—CH(CN)₂, —R¹⁰—C(=O)NR⁹R⁸, —R¹⁰—NR⁹C(=O)R⁸, —R¹⁰—NR¹¹C(=O)NR⁹R⁸, —R¹⁰—C(=S)NR⁹R⁸, —R¹⁰—CH[C(=O)R⁸]₂, —R¹⁰—CH[C(=S)R⁸]₂, —R¹⁰—CH[C(=O)OR⁸]₂, —R¹⁰—CH[C(=S)OR⁸]₂, —R¹⁰—CH[C(=O)SR⁸]₂, —R¹⁰—CH[C(=S)SR⁸]₂, or —R¹⁰—CH[C(=S)NR⁹R⁸]₂; wherein R⁸, R⁹ and R¹¹, independently of each another, represent hydrogen, alkyl, alkenyl, alkynyl, cycloalkyl, alkoxy, hydroxy, aryl or heteroaryl, which aryl or heteroaryl may optionally be substituted one or more times with alkyl, cycloalkyl, alkoxy, halogen, hydroxy, amino, trifluoromethyl, trifluoromethoxy or nitro; or R⁸ and R⁹, together with the atoms to which they are bound, form a heterocyclic ring, which heterocyclic ring may optionally be substituted one or more times with alkyl, cycloalkyl, alkoxy, halogen, hydroxy, amino, trifluoromethyl, trifluoromethoxy or nitro, and R¹¹ is as defined above; and R¹⁰ is absent or represents a linker selected from alkyl, alkenyl, alkynyl, cycloalkyl, aryl or heteroaryl.

2. The benzothiazine derivative of claim 1, wherein R¹ represents hydrogen, alkyl or cycloalkyl.

3. The benzothiazine derivative of claim 1, wherein R¹ represents hydrogen.

4. The benzothiazine derivative of claim 1, wherein R² or R³ represent cycloalkyl; and the other of R² and R³ represent hydrogen.

5. The benzothiazine derivative of claim 1, wherein R⁴ or R⁵ represent a saturated mono- or bi-cyclic heterocyclic ring having N, O and/or S as heteroatom.

6. The benzothiazine derivative of claim 5, wherein R⁴ or R⁵ represent pyrrolidinyl, pyrazolidinyl, imidazolidinyl, piperidinyl, morpholinyl, thiomorpholinyl or piperazinyl.

7. The benzothiazine derivative of claim 1, wherein R⁴ and R⁵ both represent hydrogen.

8. The benzothiazine derivative of claim 1, wherein R⁶ represents hydrogen or alkyl.

9. The benzothiazine derivative of any one of claims 1, 2, or 3, wherein
R⁷ represents —R¹⁰—S(=O)₂R⁸, —R¹⁰—S(=O)₂OR⁸, —R¹⁰—S(=O)₂NR⁹R⁸, or —R¹⁰—NR⁹S(=O)₂R⁸; wherein
R⁸ represents hydrogen or alkyl; and
R⁹ represents hydrogen or alkyl; or
R⁸ and R⁹ together with the nitrogen and/or sulphur atoms to which they are bound, form a pyrrolidine-, a piperidine-, a piperazine-, a homopiperazine-, or a morpholine ring, which heterocyclic ring is optionally substituted with alkyl or hydroxy; and
R¹⁰ is absent or represents alkyl.

10. The benzothiazine derivative of claim 9, wherein R⁷ represents
an N,N-dimethylamine-1-sulfonyl group;
a piperidine-1-sulfonyl group;
a 4-methyl-piperazine-1-sulfonyl group;
a morpholine-4-sulfonyl group; or
a 4-hydroxypiperidine-1-sulfonyl group.

11. The benzothiazine derivative of claim 1, which is
(3RS)-3-Cyclohexyl-7-(piperidine-1-sulfonyl)-3,4-dihydro-2H-benzo[e][1,2]thiazine-1,1-dioxide;
(3RS)-3-Cyclopentyl-7-(piperidine-1-sulfonyl)-3,4-dihydro-2H-benzo[e][1,2]thiazine-1,1-dioxide;
(3RS)-3-Cyclopentyl-7-(4-methyl-piperazine-1-sulfonyl)-3,4-dihydro-2H-benzo[e][1,2]thiazine-1,1-dioxide;
(3RS)-3-Cyclohexyl-7-(4-methyl-piperazine-1-sulfonyl)-3,4-dihydro-2H-benzo[e][1,2]thiazine-1,1-dioxide;
(3RS)-3-Cyclopentyl-6-methyl-7-(piperidine-1-sulfonyl)-3,4-dihydro-2H-benzo[e][1,2]thiazine-1,1-dioxide;
(3RS)-3-Cyclopentyl-6-methyl-7-(morpholine-4-sulfonyl)-3,4-dihydro-2H-benzo[e][1,2]thiazine-1,1-dioxide;
(3RS)-3-Cyclopentyl-6-methyl-7-(4-methyl-piperazine-1-sulfonyl)-3,4-dihydro-2H-benzo[e][1,2]thiazine-1,1-dioxide;
(3RS)-3-Cyclopentyl-6-methyl-7-(N,N-dimethylamine-1-sulfonyl)-3,4-dihydro-2H-benzo[e][1,2]thiazine-1,1-dioxide;
(3RS)-3-Cyclopentyl-6-methyl-7-(4-hydroxypiperidine-1-sulfonyl)-3,4-dihydro-2H-benzo[e][1,2]thiazine-1,1-dioxide;

(3RS)-3-Cyclopentyl-7-(N,N-dimethylamine-1-sulfonyl)-3,4-dihydro-2H-benzo[e][1,2]thiazine-1,1-dioxide; or (3RS)-3-Cyclopentyl-7-(morpholine-1-sulfonyl)-3,4-dihydro-2H-benzo[e][1,2]thiazine-1,1-dioxide;

or a pharmaceutically acceptable salt thereof.

12. A pharmaceutical composition comprising a therapeutically effective amount of a benzothiazine derivative of claim 1, or a pharmaceutically acceptable addition salt thereof, together with at least one pharmaceutically acceptable carrier or diluent.

13. The benzothiazine derivative of claim 11, which is (3RS)-3-cyclopentyl-6-methyl-7-(4-methyl-piperazine-1-sulfonyl)-3,4-dihydro-2H-benzo[e][1,2]thiazine-1,1-dioxide.

* * * * *